(12) United States Patent
Lin et al.

(10) Patent No.: US 11,624,067 B2
(45) Date of Patent: Apr. 11, 2023

(54) IN-VITRO INDUCTION OF ADULT STEM CELL EXPANSION AND DERIVATION

(71) Applicants: Shi-Lung Lin, Arcadia, CA (US); Samantha Chang-Lin, Arcadia, CA (US); Donald Chang, Cerritos, CA (US)

(72) Inventors: Shi-Lung Lin, Arcadia, CA (US); Samantha Chang-Lin, Arcadia, CA (US); Donald Chang, Cerritos, CA (US)

( * ) Notice: Subject to any disclaimer, the term of this patent is extended or adjusted under 35 U.S.C. 154(b) by 1240 days.

(21) Appl. No.: 16/135,723

(22) Filed: Sep. 19, 2018

(65) Prior Publication Data
US 2019/0085335 A1 Mar. 21, 2019

Related U.S. Application Data

(60) Continuation-in-part of application No. 15/661,346, filed on Jul. 27, 2017, which is a division of application No. 15/167,226, filed on May 27, 2016, now Pat. No. 9,879,263, which is a continuation-in-part of application No. 14/142,512, filed on Dec. 27, 2013, now Pat. No. 9,399,773, and a continuation-in-part of application No. 13/964,705, filed on Aug. 12, 2013, now Pat. No. 9,422,559, which is a continuation-in-part of application No. 13/572,263, filed on Aug. 10, 2012, now abandoned, said application No. 15/661,346 is a continuation-in-part of application No. 14/502,608, filed on Sep. 30, 2014, now Pat. No. 9,783,811, which is a division of application No. 13/572,263, filed on Aug. 10, 2012, now abandoned, said application No. 15/661,346 is a continuation-in-part of application No. 14/527,439, filed on Oct. 29, 2014, now Pat. No. 9,637,747, which is a division of application No. 13/572,263, filed on Aug. 10, 2012, now abandoned, said application No. 15/167,226 is a continuation-in-part of application No. 15/442,557, filed on Feb. 24, 2017, now Pat. No. 10,370,658, which is a continuation-in-part of application No. 15/167,226, filed on May 27, 2016, now Pat. No. 9,879,263, which is a continuation-in-part of
(Continued)

(51) Int. Cl.
| | |
|---|---|
| C12N 15/113 | (2010.01) |
| C12N 15/11 | (2006.01) |
| C12P 19/34 | (2006.01) |
| C12N 15/70 | (2006.01) |

(52) U.S. Cl.
CPC ........ *C12N 15/1135* (2013.01); *C12N 15/111* (2013.01); *C12N 15/113* (2013.01); *C12N 15/70* (2013.01); *C12P 19/34* (2013.01); *C12N 2310/14* (2013.01); *C12N 2310/141* (2013.01); *C12N 2320/30* (2013.01); *C12N 2320/31* (2013.01); *C12N 2330/50* (2013.01); *C12N 2330/51* (2013.01)

(58) Field of Classification Search
None
See application file for complete search history.

(56) References Cited

U.S. PATENT DOCUMENTS

| | | |
|---|---|---|
| 9,399,773 B2 | 7/2016 | Lin et al. |
| 2014/0141470 A1 | 5/2014 | Lin et al. |
| 2014/0350085 A1 | 11/2014 | Lin et al. |
| 2017/0218362 A1 | 8/2017 | Lin |

FOREIGN PATENT DOCUMENTS

| | | |
|---|---|---|
| WO | WO 2005/056797 A1 | 6/2005 |
| WO | WO 2017/095489 A1 | 6/2017 |

OTHER PUBLICATIONS

Chen, J.S.K., et al., "Recent Patents on MicroRNA-Induced Pluripotent Stem Cell Generation," Recent Patents on Regenerative Medicine, 2013, vol. 3, pp. 5-16.
Gou, D., et al., "Gou," Physiological Genomics, 2007, vol. 31, No. 3, pp. 554-562.
Lee, M.R., et al., "Epigenetic Regulation of Nanog by MiR-302 Cluster-MBD2 Completes Induced Pluripotent Stem Call Reprogramming," Stem Cells, 2013, vol. 31, pp. 666-681.
(Continued)

*Primary Examiner* — James D Schultz
(74) *Attorney, Agent, or Firm* — Birch, Stewart, Kolasch & Birch, LLP

(57) ABSTRACT

This invention generally relates to a composition and its method of use for inducing adult stem cell (ASC) expansion and/or derivation in vitro, using miR-302-like pre-miRNAs, shRNAs and/or siRNAs, all of which contain a shared sequence of 5'-UAAGUGCUUC CAUGUUU-3' (SEQ ID NO: 7) in the 5'-end, and further in conjunction with the use of some wound-healing-related defined factors, including but not limited to basic fibroblast growth factor (bFGF)/fibroblast growth factor 2 (FGF-2), leukemia inhibitory factor (LIF), insulin-like growth factor (IGF), Epidermal growth factor (EGF), platelet-derived growth factor (PDGF), vascular endothelial growth factor (VEGF), transforming growth factor (TGF), tumor necrosis factor (TNF), stem cell factor (SCF), homeobox proteins (HOX), Notch, GSK, Wnt/beta-Catenin signals, interleukins, and/or bone morphogenetic proteins (BMPs). The principle of the present invention is related to a novel mechanism of inducible symmetric ASC division recently found in a skin wound healing model in vivo. The resulting amplified ASCs are useful for treating a variety of human aging- and cell dysfunction-associated disorders, including but not limited to Alzheimer's disease, Parkinson's disease, motor neuron disease, stroke, diabetes, osteoporosis, myocardial infraction, hemophilia, anemia, AIDS, leukemia, lymphoma and many kinds of cancers as well as aging.

16 Claims, 7 Drawing Sheets
(7 of 7 Drawing Sheet(s) Filed in Color)
Specification includes a Sequence Listing.

Related U.S. Application Data application No. 14/142,512, filed on Dec. 27, 2013, now Pat. No. 9,399,773, and a continuation-in-part of application No. 13/964,705, filed on Aug. 12, 2013, now Pat. No. 9,422,559, which is a continuation-in-part of application No. 13/572,263, filed on Aug. 10, 2012, now abandoned, said application No. 15/167,226 is a continuation-in-part of application No. 14/502,608, filed on Sep. 30, 2014, now Pat. No. 9,783,811, which is a division of application No. 13/572,263, filed on Aug. 10, 2012, now abandoned, said application No. 15/167,226 is a continuation-in-part of application No. 14/527,439, filed on Oct. 29, 2014, now Pat. No. 9,637,747, which is a division of application No. 13/572,263, filed on Aug. 10, 2012, now abandoned, said application No. 15/167,226 is a continuation-in-part of application No. 15/167,219, filed on May 27, 2016, now abandoned, which is a continuation-in-part of application No. 12/792,413, filed on Jun. 2, 2010, now Pat. No. 9,394,538, and a continuation-in-part of application No. 12/149,725, filed on May 7, 2008, now Pat. No. 9,567,591, and a continuation-in-part of application No. 12/318,806, filed on Jan. 8, 2009, now abandoned, said application No. 15/167,219 is a continuation of application No. 13/964,705, filed on Aug. 12, 2013, now Pat. No. 9,422,559, and a continuation-in-part of application No. 12/792,413, filed on Jun. 2, 2010, now Pat. No. 9,394,538, and a continuation-in-part of application No. 13/572,263, filed on Aug. 10, 2012, now abandoned, application No. 16/135,723, which is a continuation-in-part of application No. 15/048,964, filed on Feb. 19, 2016, now Pat. No. 10,519,440, and a continuation-in-part of application No. 14/527,439, filed on Oct. 29, 2014, now Pat. No. 9,637,747, and a continuation-in-part of application No. 14/502,608, filed on Sep. 30, 2014, now Pat. No. 9,783,811, said application No. 14/527,439 is a division of application No. 13/572,263, filed on Aug. 10, 2012, now abandoned, said application No. 14/502,608 is a division of application No. 13/572,263, filed on Aug. 10, 2012, now abandoned.

(60) Provisional application No. 61/746,786, filed on Dec. 28, 2012, provisional application No. 61/761,890, filed on Feb. 7, 2013, provisional application No. 61/522,843, filed on Aug. 12, 2011, provisional application No. 62/262,280, filed on Dec. 2, 2015, provisional application No. 61/272,169, filed on Aug. 26, 2009, provisional application No. 61/323,190, filed on Apr. 12, 2010, provisional application No. 62/692,862, filed on Jul. 2, 2018.

(56) References Cited

OTHER PUBLICATIONS

Li, et al, Nucl. Acids. Res., 2011, vol. 39, pp. 1054-1065.
Li, et al, Stem Cells, 2011, vol. 39, pp. 1645-1649.
Akita, S., et al. "Basic Fibroblast Growth Factor in Scarless Wound Healing." Advances in Wound Care, Mar. 1, 2013, vol. 2, No. 2, pp. 44-49.
Borena, B.M., et al. "Regenerative Skin Wound Healing in Mammals: State-of-the-Art on Growth Factor and Stem Cell Based Treatments," Cellular Physiology and Biochemistry, Jan. 1, 2015, vol. 36, No. 1, pp. 1-23.
Guo. S., et al, "Factors Affecting Wound Healing," Journal of Dental Research, Feb. 5, 2010, vol. 89, No. 3, pp. 219-229.
Written Opinion of the International Searching Authority and International Search Report for Appl. No. PCT/US2018/051658 dated Feb. 25, 2019.

Example of control section shows large area of scar tissue underneath (190-CR3)

Example of treated section shows minimal scar tissue underneath (190-BR2)

IN-VITRO INDUCTION OF ADULT STEM CELL EXPANSION AND DERIVATION

PRIORITY

The present invention claims priority to the U.S. Provisional Application Ser. No. 62/692,862 filed on Jul. 2, 2018, which was entitled "In-Vitro Induction of CD34-positive Adult Stem Cell Expansion". The present application also claims priority to the U.S. patent applications Ser. No. 15/661,346 filed on Jul. 27, 2017, which was entitled "Use of MicroRNA Precursors as Drugs for Inducing CD34-positive Adult Stem Cell Expansion", to the U.S. patent applications Ser. No. 15/442,557 filed on Feb. 24, 2017, which was entitled "Composition and Method of Using miR-302 Precursors as Anti-Cancer Drug for Treating Human Lung Cancer", and to the U.S. patent applications Ser. No. 15/048,964 filed on Feb. 19, 2016, which was entitled "A Composition and Method of Using miR-302 Precursors as Drugs for Treating Alzheimer's Diseases". The present application is a continuation-in-part (CIP) application of the U.S. patent applications Ser. No. 15/661,346 filed on Jul. 27, 2017, which was entitled "Use of MicroRNA Precursors as Drugs for Inducing CD34-positive Adult Stem Cell Expansion", the U.S. patent applications Ser. No. 15/442,557 filed on Feb. 24, 2017, which was entitled "Composition and Method of Using miR-302 Precursors as Anti-Cancer Drug for Treating Human Lung Cancer", and the U.S. patent applications Ser. No. 15/048,964 filed on Feb. 19, 2016, which was entitled "A Composition and Method of Using miR-302 Precursors as Drugs for Treating Alzheimer's Diseases", all of which are hereby incorporated by reference as if fully set forth herein.

REFERENCE TO SEQUENCE LISTING SUBMITTED VIA EFS-WEB

This application includes an electronically submitted sequence listing in .txt format. The .txt file contains a sequence listing entitled "2018 Nov. 27 SequenceListing 5199-0246PUS1.txt" created on Nov. 20, 2018 and is 3,097 bytes in size. The sequence listing contained in this .txt file is part of the specification and is hereby incorporated by reference herein in its entirety.

FIELD OF INVENTION

This invention generally relates to a composition and its method of use for inducing adult stem cell (ASC) expansion and/or derivation in vitro using certain small non-coding RNAs (snRNA) in conjunction with some defined protein factors, including small hairpin-like RNA (shRNA), microRNA precursors (pre-miRNA) and/or short interfering RNAs (siRNA) in conjunction with one or more defined factors consisting of basic fibroblast growth factor (bFGF)/ fibroblast growth factor 2 (FGF-2), leukemia inhibitory factor (LIF), insulin-like growth factor (IGF), Epidermal growth factor (EGF), platelet-derived growth factor (PDGF), vascular endothelial growth factor (VEGF), transforming growth factor (TGF), tumor necrosis factor (TNF), stem cell factor (SCF), homeobox proteins (HOX), Notch, GSK, Wnt/beta-Catenin signals, interleukins, and/or bone morphogenetic proteins (BMPs). Particularly, the present invention relates to a composition and its method of use for inducing CD34-positive adult stem cell (CD34$^+$ASC) expansion and/or derivation in vitro, using miR-302-mimic shRNAs, pre-miRNAs and/or siRNAs, containing a shared sequence homologous to 5'-UAAGUGCUUC CAUGUUU-3' (SEQ ID NO: 7), and further in conjunction with the use of one or more defined factors selected from bFGF/FGF-2, LIF, IGF, EGF, PDGF, VEGF, TGF, TNF, SCF, HOX, Notch, GSK, Wnt/ß-Catenin, interleukins and/or BMPs. The principle of induced ASC expansion and derivation is related to a novel mechanism of inducible symmetric adult stem cell division recently found in a skin wound healing model in vivo. The resulting amplified ASCs are useful for treating a variety of human aging- and cell dysfunction-associated disorders, including but not limited to Alzheimer's disease, Parkinson's disease, motor neuron disease, stroke, diabetes, osteoporosis, myocardial infraction, hemophilia, anemia, AIDS, leukemia, lymphoma and many kinds of cancers. Notably, the present invention is also useful for preventing aging as well as treating aging-related degenerative discomforts by supplying unlimited amplified self-ASCs to the body, so as to repair and rejuvenate the damaged and/or aged tissues and organs in vivo.

BACKGROUND

Stem cells resemble a treasure box of life containing numerous effective ingredients useful for stimulating new cell/tissue regeneration, repairing and/or rejuvenating damaged/aged tissues, treating degenerative diseases, and preventing tumor/cancer formation and progression. Hence, it is conceivable that we can use these stem cells as a tool for novel drug screening, identification, isolation, and production. As a result, the drugs so obtained may be useful for developing pharmaceutical and therapeutic applications, such as a biomedical utilization, device and/or apparatus for research, diagnosis, and/or therapy use, and a combination thereof.

MicroRNA (miRNA) is one of the main effective ingredients in human embryonic stem cells (hESCs). Major hESC-specific miRNAs include but not limited to members of the miR-200, miR-290~295, miR-302, miR-371~373, and miR-520 families. Among them, the miR-302 family has been found to play a crucial role in pluripotency maintenance and tumor suppression (Lin and Ying, 2008; Lin et al., 2008, 2010 and 2011). MiR-302 contains eight (8) familial members, including four (4) sense miR-302 (a, b, c, and d) and four (4) antisense miR-302* (a*, b*, c*, and d*) sequences. These sense and antisense members are partially complementary to each other and can form double helix conformations, respectively. For example, precursors of miR-302 are hairpin-like small RNAs formed by duplexes (stem arms) of miR-302a and a* (pre-miR-302a; SEQ.ID.NO.1), miR-302b and b* (pre-miR-302b; SEQ.ID.NO.2), miR-302c and c* (miR-302c; SEQ.ID.NO.3), and miR-302d and d* (pre-miR-302d; SEQ.ID.NO.4), respectively, with a linked nucleotide sequence in one end (stem loop). In order to activate miR-302 function, miR-302 precursors (pre-miR-302s) are first processed into mature miR-302 and miR-302* by cellular RNase III Dicers and further form RNA-induced silencing complexes (RISCs) with certain Argonaute (AGO) proteins, subsequently leading to either RNA interference (RNAi)-directed degradation or translational suppression of targeted gene transcripts (mRNAs), in particular developmental gene and oncogene mRNAs (Lin et al., 2008, 2010 and 2011).

MiR-302 is the most abundant non-coding RNA (ncRNA) species in hESCs and induced pluripotent stem cells (iPSCs). Our previous studies have shown that ectopic overexpression of miR-302 beyond the level found in hESCs is able to reprogram both of human normal and cancerous tissue cells to hESC-like iPSCs with a relatively slow cell cycle rate (20-24 hours/cycle) similar to that of a morula-stage early human zygote (Lin et al., 2008, 2010 and 2011; EP 2198025, U.S. Pat. Nos. 9,567,591, 9,394,538, and U.S. patent application Ser. No. 12/318,806 to Lin). Relative quiescence is a defined characteristic of these miR-302-induced iPSCs, whereas hESCs and other previously reported four-factor-induced (either Oct4-Sox2-K1f4-c-Myc or Oct4-Sox2-Nanog-Lin28) iPSCs show a highly proliferative cell cycle rate (12-15 hours/cycle) similar to that of a tumor/cancer cell (Takahashi et al., 2006; Yu et al., 2007; Wernig et al., 2007; Wang et al., 2008). To study the tumor suppression effect of miR-302, we have identified the involvement of two miR-302-targeted G1-checkpoint regulators, including cyclin-dependent kinase 2 (CDK2) and cyclin D (Lin et al., 2010; U.S. Pat. Nos. 9,394,538 and 9,422,559 to Lin). It is known that cell cycle progression is driven by activities of cyclin-dependent kinases (CDKs), which forms functional complexes with positive regulatory subunits, cyclins, as well as by negative regulators, CDK inhibitors (CKIs, such as p14/p19Arf, p15Ink4b, p16Ink4a, p18Ink4c, p21Cip1/Waf1, and p27Kip1). In mammals, different cyclin-CDK complexes are involved in regulating different cell cycle transitions, such as cyclin-D-CDK4/6 for G1-phase progression, cyclin-E-CDK2 for G1-S transition, cyclin-A-CDK2 for S-phase progression, and cyclin-A/B-CDC2 (cyclin-A/B-CDK1) for entry into M-phase. As a result, our studies have demonstrated that the tumor suppression function of miR-302 results from co-suppression of the cyclin-E-CDK2 and cyclin-D-CDK4/6 pathways during G1-S transition.

Although miR-302 is useful for designing and developing novel anti-cancer drugs/vaccines, its production is problematic because natural miR-302 and its precursors can only be found in human pluripotent stem cells, particularly hESCs, of which the resource is very limited. Alternatively, synthetic small interfering RNAs (siRNA) may be used to mimic natural miR-302 precursors (pre-miR-302); yet, since the stem-arm region of a hairpin-like pre-miR-302 structure is formed by two imperfectly complementary strands of sense miR-302 and antisense miR-302*, the synthetic perfectly matched siRNA-302 mimics can not replace the function of native miR-302*, of which the sequence is different from the antisense strand of siRNA. For example, the antisense strand of siRNA-302a mimic is 5'-UCAC-CAAAAC AUGGAAGCAC UUA-3' (SEQ.ID.NO.5), whereas native miR-302a* is 5'-ACUUAAACGU GGAU-GUACUU GCU-3' (SEQ.ID.NO.6). As the full miR-302 function results from both of its sense miR-302 and antisense miR-302* strands, previous reports using those siRNA mimics often showed some different results from the real native miR-302 function. Furthermore, due to the high degree (23%~46%) of mismatched nucleotides existing between sense miR-302 and antisense miR-302* sequences, synthetic miR-302 and miR-302* are not likely to form any correct hybrid duplex in nature, particularly without the help of a stem-loop structure. The function of a pre-miRNA stem-loop structure is to bring the two mismatched sense and antisense miRNA sequences close and long enough to form a stable and correct hybrid duplex conformation. On the other hand, our recent discovery of iPSCs may provide an alternative source for pre-miR-302 production (EP 2198025, U.S. Pat. No. 9,567,591 and U.S. patent application Ser. No. 12/318,806 to Lin). Nevertheless, the cost of growing these iPSCs is still too high to be used for industrial production.

In addition to iPSC generation, our recent studies have further discovered that miR-302 can also induce CD34-positive adult stem cell (CD34$^+$ASC) expansion and derivation in vivo (U.S. Pat. No. 9,879,263 and U.S. patent application Ser. No. 15/661,346 to Lin). Prior arts attempting to expand adult stem cell (ASC) populations include U.S. Pat. No. 7,850,960 to Moon using GSK-3, U.S. Pat. No. 8,372,397 and European Patent No. EP2415480A2 to Moon using the Wnt/ß-Catenin signaling pathway, U.S. patent application Ser. No. 11/614,345 to Rudd using G-CSF/GM-CSF plus SCF, and U.S. patent application Ser. No. 13/266,428 to Rudnicki using Wnt7a. Moreover, several scientific reports have also indicated the involvement of HOXB4 and Notch1/4 in inducing human CD34-positive hematopoietic stem cell (HSC) expansion ex vivo (Antonchuk et al, Cell 109: 39-45, 2002; Karlsson S. Blood 104: 2210-2211, 2004; Schiedlmeier et al, PNAS USA 104: 16952-16957, 2007). Furthermore, Miller et al. (PNAS USA 94: 13648-13653, 1997) have further demonstrated the induction of murine (CD34-negative) HSC expansion in vitro using IL-6/11, flt3-ligand and Steel factor (SF). Nevertheless, as described in a recent review summarized by Walasek et al (Ann. N.Y. Acad. Sci. 1266: 138-150, 2012), it stated that "Attempts to improve hematopoietic reconstitution and engraftment potential of ex vivo—expanded hematopoietic stem and progenitor cells (HSPCs) have been largely unsuccessful due to the inability to generate sufficient stem cell numbers and to excessive differentiation of the starting cell population. Although hematopoietic stem cells (HSCs) will rapidly expand after in vivo transplantation, experience from in vitro studies indicates that control of HSPC self-renewal and differentiation in culture remains difficult. Protocols that are based on hematopoietic cytokines have failed to support reliable amplification of immature stem cells in culture, suggesting that additional factors are required." Particularly, it is noted that these expanded ASCs can not be repeatedly cultivated for multiple passages in vitro or ex vivo. As a result, all these prior arts can merely provide a maximally ten to few hundred fold amplification of the starting ASC populations, which are not sufficient to be used in clinical therapy.

In view of the low amplification rate and poor multipotent quality of prior ASC expansion methods, it is desirable to have a novel solution for overcoming these problems. Clearly, as stated by Walasek, an additional key factor may be required for fulfilling this task, albeit no one knows what is the factor before. To this, our recent studies have identified a novel key factor capable of overcoming all the prior art problems, using a small microRNA (miRNA), miR-302, rather than a protein. The prior arts overlook this miRNA because they do not know its DNA demethylation function, which is required for unlocking the natural barriers, such as gene methylation and histone acetylation, in the cell genome, so as to activate the full mechanism of gene regulation processes required for inducing ASC expansion and/or derivation under a variety of in-vitro, ex-vivo and in-vivo conditions.

SUMMARY OF THE INVENTION

The principle of the present invention is mainly relied on the DNA demethylation function of miR-302. Conceivably, other small RNAs, such as shRNA, siRNA and hairpin-like pre-miRNA, or chemicals as well as protein factors with a similar function may be used to replace miR-302 for the same purpose of inducing DNA demethylation in cells and so as to activate ASC expansion and/or derivation in vitro, ex vivo as well as in vivo. It is well known that stem cells contain a highly demethylated genome in order to preserve and maintain their pluripotency (i.e. hESCs and iPSCs) or multipotency (i.e. ASCs). In the cell genome, DNA methylation serves as a lock to set up all kinds of cell-type-specific gene expression profiles and hence prohibiting any possible reverse development or reprogramming of somatic cells back to stem cells. As a result, DNA demethylation is the most important key step required for unlocking the genome and resetting the gene expression patterns to a unique stem cell-specific profile, so as to induce and maintain pluripotency or multipotency during stem cell renewal and/or reprogramming. To study this DNA demethylation process, we are the first scientists who found the mechanism of miR-302-mediated DNA demethylation in hESCs and iPSCs (Lin and Ying, 2008; Lin et al., 2008 and 2011; Ying et al., 2018). Our previous studies have revealed that miR-302 can down-regulate multiple key epigenetic regulators, such as MECP1/2, AOF1/2 (or called KDM1b/1a or LSD2/1), DNMT1, HDAC2/4 and MBD2, to facilitate genomic DNA demethylation and iPSC reprogramming (Lin and Ying, 2008; Lin et al., 2008, 2011, and 2013). By the same token, miR-302 may be able to down-regulate all or some of these key epigenetic regulators to induce and maintain ASC renewal and expansion.

The strength of microRNA (miRNA)-mediated gene regulation is dependent on the miRNA concentration and the affinity between the miRNA and its targeted genes. In other words, strong target genes will present a higher affinity to the miRNA and thus requires a lower miRNA concentration to be silenced, and vice versa. As a result, different target genes will be down-regulated at different levels of the miRNA concentration used. For example, we have found that the use of a higher miR-302 concentration (higher than the miR-302 levels of hESCs H1 and H9 lines) can induce somatic cell reprogramming to form hESC-like iPSCs (Lin et al., 2008, 2010 and 2011; EP 2198025, U.S. Pat. Nos. 9,567,591, 9,394,538, U.S. patent application Ser. No. 12/318,806 to Lin), while our recent inventions also showed that the use of a relatively lower miR-302 concentration (about 10%~50% of the miR-302 levels in hESCs H1 and H9) induces CD34+ASC expansion in vivo (U.S. Pat. No. 9,879,263 and U.S. patent application Ser. No. 15/661,346 to Lin). This evidence suggests that the mechanisms of these two distinct events are likely different from each other and may involve slightly different sets of the miR-302-targeted genes. Particularly, because the use of merely miR-302 can only induce CD34+ASC expansion under a wound healing condition in vivo, but not in a cell culture in vitro, it is conceivable that other defined factors involved in wound healing may be also required for functioning together with miR-302 in order to set up the ASC-specific gene profile needed for inducing ASC expansion and/or derivation in vitro. These wound healing-related defined factors may include but not limited to basic fibroblast growth factor (bFGF)/fibroblast growth factor 2 (FGF-2), leukemia inhibitory factor (LIF), insulin-like growth factor (IGF), Epidermal growth factor (EGF), platelet-derived growth factor (PDGF), vascular endothelial growth factor (VEGF), transforming growth factor (TGF), tumor necrosis factor (TNF), stem cell factor (SCF), homeobox proteins (HOX), Notch, GSK, Wnt/B-Catenin pathway signals, interleukins, and/or bone morphogenetic proteins (BMPs).

The miR-302 family is the most abundant miRNA species in hESCs and iPSCs. All the sense miR-302 familial members share an identical consensus sequence in their 5'-end seventeen (17) nucleotides, 5'-UAAGUGCUUC CAU-GUUU-3' (SEQ.ID.NO.7), and contain >82% homology in their full-length 23-nucleotide mature sequences. Based on the analysis results predicted by online computing programs TARGETSCAN (http://www.targetscan.org/) and PICTAR-VERT (http://pictar.mdc-berlin.de/), these sense miR-302 members include miR-302a (SEQ.ID.NO.8), miR-302b (SEQ.ID.NO.9), miR-302c (SEQ.ID.NO.10), and miR-302d (SEQ.ID.NO.11), all of which can concurrently target against almost over 98% the same genes, including >600 human genes. In addition, miR-302 also shares many overlapping target genes with miR-92, miR-93, miR-200, miR-367, miR-371, miR-372, miR-373, miR-374, and miR-520 familial members, all of which may possess similar functions. The majority of these target genes are developmental signals and/or transcriptional factors involved in initiating or establishing cell-lineage-specific differentiation during early embryogenesis (Lin et al., 2008 and 2011; Ying et al., 2018). Many of these target genes are also oncogenes; hence, miR-302 and its related miRNAs may further function as a tumor suppressor to prevent the wrong deviation of normal stem cell renewal or expansion into tumor/cancer cell formation.

Stem cell research holds the key for developing novel regenerative medicine. To this, our studies focus on screening, discovering and isolating new medicines from stem cells for treating a variety of human diseases. The debut of iPSCs has greatly advanced our progress in this research direction. Using iPSCs, we have isolated and identified "glycylglycerins" as a group of novel sugar-like chemicals that protect embryonic-stem-cell-specific miRNAs (ESC-miRNAs), including miR-302, from degradation and hence preserve their functions for maintaining the pluripotency of iPSCs and ESCs (U.S. Pat. No. 9,387,251 to Lin). Our recent studies (Lin SL, 2018) have further demonstrated that some of the isolated glycylglycerin-bound ESC-miRNAs, particularly miR-302, can be used to enhance scar-less (or called perfect) wound healing via inducing CD34-positive adult stem cell (CD34+ASC) expansion in vivo. Since there is no report of any similar mechanism before, the present invention herein provides the first evidence for: (1) the novel function of miR-302 and other wound-healing-related defined factors involved in the ASC expansion mechanism in vivo as well as in vitro, (2) the first reconstitution model for inducing CD34+ASC expansion in vitro, and (3) the possible somatic tissue cell types derived from the resulting induced CD34+ASCs (iCD34+ASCs). The present invention of induced CD34+ASC expansion and derivation in vitro offers the ability to provide unlimited and sufficient patient's own adult stem cells in vitro for performing auto-transplantation therapies in vivo to treat a variety of human diseases, including but not limited to Alzheimer's disease, Parkinson's disease, motor neuron disease, stroke, diabetes, osteoporosis, myocardial infraction, hemophilia, anemia, AIDS, leukemia, lymphoma, and many kinds of cancers, as well as aging. Auto-transplantation is the best way of stem cell therapy to prevent immune rejection. As a result, the present invention will surely lay a solid foundation for advancing the breakthrough development of novel stem cell therapies, leading to a significant impact on future regenerative medicine.

Induced In-Vivo ASC Expansion Models.

Our first inducible ASC expansion model in vivo was established in 2011 using miR-302 precursors (pre-miR-302) isolated from iPSCs. Using a mouse skin wound healing model, we observed the formation of ASC-like expansion pouch (yet CD34 negative) in vivo after pre-miR-302 treatments (Chen et al., 2013; Lin SL, 2018). As CD34 is a valid stem cell marker for human and pig ASCs, but not mouse ASCs, we herein established another pig skin wound healing model in 2014, using the same treatment methodology, which showed similar pouch-like CD34+ASC expansion in vivo (FIGS. 1 to 5). As a result, we currently have both of pig (CD34-positive) and mouse (CD34-negative) ASC expansion models for studying the mechanism of ASC expansion and derivation in vivo, ex vivo as well as in vitro.

Wound healing is the best in-vivo model to study ASC activities. In old theory, ASCs can divide asymmetrically to give rise to one copy of itself (ASC) and the other differentiated daughter cell (called progenitor cell), of which the progenitor cell can be further divided and differentiated into various kinds of new tissue cells for repairing the damaged tissues. Hence, a perfect (scar-less) wound healing event requires sufficient ASCs to provide abundant new tissue cells for fully repairing and recovering all the wounded tissue areas. In this scenario, how to maintain the homeostasis of a sufficient ASC population in vivo is the key step. Nevertheless, the old "asymmetric stem cell division" theory can not maintain such ASC homeostasis because there are so many internal and environmental risks that are able to damage ASCs, including but not limited to pollution, poison, radiation, stress, injury, illness, and even aging. To overcome this problem, we tried to use the DNA demethylation function of miR-302 to induce and/or enhance symmetric ASC division.

Using a pig skin wound healing treatment model in vivo (FIGS. 1 and 3), we found that both of the treatments of isolated pre-miR-302 (miR-302) and iPSC lysate can induce fast and scar-less wound healing in all tested samples in vivo (n=12/12 for each group), compared to the results of untreated controls and other control treatments of miR-434-mimic siRNAs (miR-434). For more details, FIG. 5 further shows the histological result of scar-less wound healing after miR-302 treatments (i.e. sample 190-BR2) compared to that of untreated controls (i.e. sample 190-CR3). After all quantitative measurements, the line chart of FIG. 4 summarizes the time-course wound closure rates of different treatment groups of FIG. 3, respectively. Since iPSC lysate also contains a high amount of miR-302, it shows that both of the miR-302 and iPSC lysate treatments achieve a high 90% wound closure rate in the 11th day, whereas other control treatments still need 6 more days (17th day) to reach the same healing result. Most importantly, during the first 3 day wound healing period, both of the miR-302- and iPSC lysate-treated samples have already shown ≥10%~20% wound contraction, which is the most crucial key step required for scar-less wound healing! Wound contraction is well known to be the key phase of tissue repairing during healing and thus any delay in wound contraction will result in disfigurement and scar formation in the healed tissues.

Using immunohistochemical (IHC) staining with a green fluorescent anti-CD34 antibody (FIG. 5), we identified a regular distribution pattern of expanded CD34+ASC pouches in both of the miR-302- and iPSC lysate-treated skins, but not in the untreated or miR-434-treated samples. Each of these expansion pouches contains approximately ≥20~1200 CD34+ASCs. Because asymmetric stem cell division can not create such many ASC expansion pouches, they must result from a "symmetric stem cell division" mechanism induced by miR-302 treatments. Notably, these CD34+ ASC pouches are regularly distributed across the junction areas of dermis and epidermis layers and usually keep a distant of about 240~290 μm away from each other, not randomly, indicating that the induced CD34+ASCs are specifically multiplied and expanded from original ASCs in the skin tissues rather than a random somatic cell reprogramming event. Untreated samples also show the same distance between two single CD34+ASCs, but without any sign of ASC expansion in the healed tissue areas. This regular distance between two ASCs may represent a complete network of repairing and recovery systems in skin tissues.

In view of the results shown in FIGS. 1-5, our studies have established that (1) the miR-302 treatments increase wound closure rates over 70~90% faster than that of conventional antibiotic ointment treatments (FIGS. 3 and 4), (2) the miR-302 treatments result in very minor scar or scar-less wound healing in all tested samples (n=12/12) (FIGS. 3-5), and (3) the miR-302 treatments induce CD34+ASC expansion over 20~1000 fold increases in vivo in all treated samples (n=12/12) (FIG. 5). Based on these findings, we herein conclude that the use of miR-302 under a wound healing condition is required for inducing and maintaining CD34+ASC expansion in vivo, so as to facilitate the result of perfect wound healing. Conceivably, the combinational use of miR-302 and certain wound healing-related factors may be able to induce and maintain ASC expansion in vitro as well. However, since there are many wound healing-related factors in vivo, the individual significance of their functional roles in the mechanism of ASC expansion remains to be determined. To this, the present invention has revealed some of these defined factors.

To identify the defined factors involved in ASC expansion, we have further performed laser capture micro-dissection (LCM) and gene microarray analyses to study the gene profiles of isolated CD34+ASCs and the related gene regulation mechanisms of ASC expansion in vivo (FIGS. 1 and 2). Based on the gene profiles identified, we found that the processes (steps) of induced ASC expansion and derivation include: (1) miR-302 down-regulates several key epigenetic genes, particularly MECP1/2 and HDAC2/4, to set up a specific DNA demethylation pattern in the cell genome, (2) the specific DNA demethylation pattern then induces the expression of a specific set of symmetric stem cell division (SSCD)-associated genes and thus activates their downstream signaling pathways, and (3) the induced SSCD-associated genes and the wound healing-related defined factors then work together to stimulate and maintain the ASC expansion; yet, most importantly, they must continuously remain working together under the specific DNA demethylation condition in order to fully complete the whole mechanism of ASC expansion and derivation. In view of this newly established mechanism, all prior art methods had clearly failed to provide such a specific DNA demethylation condition for maintaining ASC expansion in vitro or ex vivo and thus can not produce sufficient amplified ASCs for clinical therapy. To overcome this problem, the present invention is the first method using miR-302-mediated DNA demethylation to set up the required condition for working together with the wound healing-related defined factors, so as to complete the full processes of ASC expansion and derivation in vitro.

Induced In-Vitro CD34+ASC Expansion Models.

Using LCM and microarray analyses (FIGS. 1, 2 and 6), we had identified several defined factors for inducing CD34+ASC expansion in vitro. The starting CD34+ASCs can be isolated from enzymatically dissociated skin cells from either humans or pigs (FIG. 6, upper panels). Under a feeder-free MSC Expansion culture condition supplemented with the identified defined factors (such as bFGF/FGF2, LIF, and some other optional wound healing related factors), we found that the treatment of miR-302 or its siRNA/shRNA mimics can induce multiplication of isolated skin CD34+

ASCs over 20~100 folds (about ≥6~8 cell divisions in one cell culture passage) per treatment in vitro. By renewing the cell culture medium supplemented with fresh miR-302, LIF, bFGF/FGF2, and/or other optional defined factors every 3~4 days, we can repeatedly cultivate these induced CD34$^+$ ASCs (iCD34$^+$ASCs) for over 5~6 passages and eventually reach an over 10~100 million fold net CD34$^+$ASC increase in vitro. LIF is one of the identified SSCD-associated genes required for ASC expansion, while the other optional healing-related defined factors may enhance the effect of miR-302-induced ASC expansion, but not required, including IGF, EGF, PDGF, VEGF, TGF, TNF, SCF, HOX, Notch, GSK, Wnt/B-Catenin, interleukins and/or BMPs.

Most interesting, all of these expanded iCD34$^+$ASCs are surrounded by a thin layer of CD34$^+$ASC-derived membrane (weak or no CD34 expression) and hence do not directly contact with other CD34-negative tissue cells (FIG. 6, lower left panels). As a result, we can easily separate and collect the pure iCD34$^+$ASC colonies for further multiplication. Up to date, we have successfully cultivated and maintained the expanded iCD34$^+$ASCs for over 10 passages without any detectable change in karyotyping. After that, removing miR-302 from the cell culture medium pauses iCD34$^+$ASC division but not affect the cell viability (FIG. 6, lower right panels). Under different cell culture conditions by missing a certain defined factor in the culture medium, the iCD34$^+$ASCs can be further differentiated into several kinds of different tissue cell types, particularly in the ectoderm lineage in vitro (FIG. 6, lower right panels including neuronal and skin cell types). For example, when removing both miR-302 and bFGF/FGF2, they are differentiated into neuronal cells. Alternatively, when removing both miR-302 and LIF, they are differentiated into skin-type tissue cells. Further transplantation of the isolated iCD34$^+$ASCs into nude mice forms various tissue cell types in vivo, particularly in the ectoderm and mesoderm lineages (FIG. 7). In view of these findings, we herein conclude that the combinational use of miR-302 and certain defined factors can induce and maintain ASC expansion as well as derivation in vitro, leading to a novel method for generating abundant and sufficient induced CD34$^+$ASCs useful for a variety of cell therapies using either the amplified ASCs or the ASC-differentiated tissue cells, or both.

As previous studies in mouse and rat ESC renewal had reported that the use of LIF/STAT3 and BMP4/Id proteins can sustain in-vitro ESC renewal without the need of serum or feeders (Ying et al., 2003; Xu et al., 2005), our recent finding of LIF function to induce CD34$^+$ASC expansion may suggest a similar or parallel mechanism shared by both of the ESC and ASC renewal systems. Based on this scenario, we found that LIF blocks CD34$^+$ASC differentiation into the mesoderm lineage, whereas bFGF/FGF2 prevents CD34$^+$ASC differentiation into the neuron-ectoderm lineage. As a result, the synergistic activities of LIF and bFGF/FGF2 cancel all differentiation possibilities of CD34$^+$ ASCs and so as to maintain their stem cell multipotency. Nevertheless, unlike ESCs, most of ASCs do not co-express strong Oct3/4 and Nanog to bypass replicative senescence. Hence, how can ASCs bypass replicative senescence to reach a long unlimited life cycle is the key question here. To this, since our previous studies (Lin et al., 2011; Lin and Ying, 2013) has further shown that miR-302 can directly silence AOF2/KDM1, DNMT1 and HDAC2/4 to enhance the telomerase reverse transcriptase (TERT) activity and thus prevents iPSC senescence, we herein suggest that the microarray-identified SSCD genes in our present invention, including but not limited to AOF2/KDM1, DNMT1, HDAC2/4 and their downstream TERT, likely function to prevent iCD34$^+$ASC senescence and so as to extend the replicative life and passages of iCD34$^+$ASCs in the cell culture in vitro.

In-Vivo Transplantation Model showing the Multipotent Derivation of iCD34$^+$ASCs.

We believe that the intrinsic environments in different tissues/organs may guide and affect the cell fates of iCD34$^+$ ASC differentiation in vivo. For testing iCD34$^+$ASC differentiation, we adopted an in-vivo transplantation model using NOD-SCID mice (n=3). Also, in order to tracking the cell distribution and differentiation in vivo, we labeled these iCD34$^+$ASCs with a red fluorescent protein (RFP)-expressing lentiviral vector pLVX-EF1a-HcRed-N1 (Clontech) and then selected the resulting RFP-positive CD34$^+$ASCs with flow cytometry. After that, the transplantation was accomplished by injecting approximately $5 \times 10^5$ RFP-labeled iCD34$^+$ASCs into the tail vein of each NOD-SCID mouse. Following 3-week post-transplantation, we observed that numerous RFP-positive CD34$^+$ASCs and their differentiated cells survived and continued to grow in many tissues and organs in vivo, including bone marrow, brain, heart, lung, spleen, thyroid, . . . etc, most of which are derived from either ectoderm or mesoderm but rarely from endoderm lineage. As a result, FIG. 7 clearly shows that the implanted CD34$^+$ASCs and their differentiated tissue cells were abundantly located in bone marrow, brain, and thyroid tissues in vivo.

Most notably, the implanted iCD34$^+$ASCs can remain viable and further form many stem cell pouches/niches in bone marrow, where hematopoietic stem cells (HSCs) are also located. However, it is currently unclear whether or how these two kinds of CD34$^+$ASC types are related? Since many differentiated RFP-positive blood cells can be found in the peripheral blood stream even over 3 weeks after transplantation, identified using blood smear examination under a fluorescent microscope, it suggests that the implanted iCD34$^+$ASCs can be differentiated into at least some types of blood cells in vivo. Conceivably, if the physiological function of HSCs and the implanted iCD34$^+$ASCs are interchangeable in respect of providing various hematopoietic cell types for the body in vivo, we may be able to use patients' own iCD34$^+$ASCs to treat many blood-related diseases, particularly including but not limited to stroke, myocardial infraction, AIDS, leukemia, lymphoma, and sickle cell anemia. This kind of autotransplantation is also the best way of therapy to prevent immune rejection.

Furthermore, as shown in FIG. 7, the finding of iCD34$^+$ ASC pouches and the related RFP-positive neuron cells in brain is another important evidence for developing novel therapies useful for treating a variety of degenerative neuron-related disorders, particularly including but not limited to stroke, diabetes dementia, Alzheimer's, Parkinson's and motor neuron diseases.

Current knowledge about ASC lifespan and their special ways of cell division regulation (i.e. asymmetric versus symmetric stem cell division) is extremely limited. Also, it is unclear how many differences and/or similarities exist between HSCs and other CD34$^+$ASC types. To solve these questions, our current in-vitro and in-vivo CD34$^+$ASC expansion models shown in the present invention can be served as a useful tool for studying these interesting points. Using these newly established iCD34$^+$ASC expansion models, we have found that (1) miR-302 can function to induce CD34$^+$ASC expansion in vivo, which plays a crucial role in perfect wound healing, (2) the use of miR-302 and certain defined factors, such as bFGF/FGF2 and LIF, can induce CD34+ASC expansion in vitro, providing abundant amplified iCD34+ASCs for research and medical use, (3) in-vivo transplantation of the expanded iCD34+ASCs can grow and form a variety of differentiated tissue cells in many organs/tissues, indicating the multipotency of these iCD34+ASCs, particularly in the ectoderm and mesoderm lineages, and (4) the transplanted iCD34+ASCs can grow and form pouch-like stem cell niches in bone marrow, brain, spleen and thyroid, showing a great potential for developing novel regenerative medicine and therapy useful for treating Alzheimer's disease, Parkinson's disease, motor neuron disease, stroke, diabetes, osteoporosis, myocardial infraction, hemophilia, anemia, AIDS, leukemia, lymphoma and many kinds of cancers as well as aging.

A. Definitions

To facilitate understanding of the invention, a number of terms are defined below: Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more DNAs and/or RNAs, preferably more than three, and usually more than ten. An oligonucleotide longer than 13 nucleotide monomers is also called polynucleotiude. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification, which may be selected from the group consisting of mRNA, hnRNA, rRNA, tRNA, snoRNA, snRNA, pre-microRNA, viral RNA and their RNA precursors as well as derivatives.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" or "*" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding.

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3" can form complete base pairing with its antisense sequence "5'-A-C-G-A-T-3".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3" is complementary to the sequence "5'-A-C-T-3", and also to "5'-A-C-U-3". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenecity, cancer cell apoptosis, and a combination thereof.

Non-coding RNA (ncRNA): an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts (mRNAs) that have partial complementarity to the sequence of microRNA. Mature microRNA is usually sized about 17-27 oligonucleotides in length and is able to either directly degrade its intracellular mRNA target(s) or suppress the protein translation of its targeted mRNA(s), depending on the complementarity between the microRNA and its target mRNA(s). Native microRNAs are found in almost all eukaryotes, functioning as a defense against viral infections and allowing regulation of specific gene expression during development of plants and animals. In principle, one microRNA often target multiple target mRNAs to fulfill its full functionality while on the other hand multiple miRNAs may target the same gene transcripts to enhance the effect of gene silencing.

MicroRNA Precursor (Pre-miRNA): hairpin-like single-stranded RNA containing stem-arm and stem-loop regions for interacting with intracellular RNase III Dicer endoribonucleases to produce one or multiple mature microRNAs (miRNAs) capable of silencing a targeted gene or a specific group of targeted genes that contain full or partial complementarity to the mature microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with some argonaute proteins (AGO).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, or perhaps binds to, and initiates RNA transcription. For the purposes of the instant invention, a promoter can be a known polymerase or its cofactor binding site, an enhancer and the like, any sequence that can initiate synthesis of RNA transcripts by a desired polymerase.

Cistron: a sequence of nucleotides in a DNA molecule coding for an amino acid residue sequence and including upstream and downstream DNA expression control elements.

Intron Excision: a cellular mechanism responsible for RNA processing, maturation and degradation, including RNA splicing, exosome digestion, nonsense-mediated decay (NMD) processing, and a combination thereof.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf, p15Ink4b, p16Ink4a, p18Ink4c, p21Cip1/Waf1, and p27Kip1, and a combination thereof.

Tumor Suppression Effect: a cellular anti-tumor and/or anti-cancer mechanism and response consisting of, but not limited, cell cycle attenuation, cell cycle arrest, inhibition of tumor cell growth, inhibition of cell tumorigenecity, inhibition of tumor/cancer cell transformation, induction of tumor/cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Gene Silencing Effect: a cell response after a gene function is suppressed, consisting of, but not limited, inhibition of oncogene expression, inhibition of cell proliferation, cell cycle arrest, tumor suppression, cancer regression, cancer prevention, cell apoptosis, cell repairing and/or rejuvenation, cell reprogramming, reprogramming diseased cells to a relatively normal state (spontaneous healing), and a combination thereof.

Cancer Reversion: a reprogramming mechanism that resets the malignant properties of high-grade cancers back to a relatively normal-like low-grade state in vitro, ex vivo or in vivo.

Antibody: a peptide or protein molecule having a pre-selected conserved domain structure coding for a receptor capable of binding a pre-selected ligand.

Human Degenerative Diseases (HDD): HDD includes but not limited to Alzheimer's disease, Parkinson's disease, motor neuron disease, stroke, diabetes, osteoporosis, myocardial infraction, hemophilia, anemia, leukemia, lymphoma, and many kinds of cancers as well as aging-associated disorders.

Pharmaceutical and/or Therapeutic Application: a biomedical utilization, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

B. Compositions and Applications

A composition and its method of use for inducing adult stem cell (ASC) expansion and/or derivation in vitro, using miR-302-like pre-miRNAs, shRNAs and/or siRNAs, all of which contain a shared sequence of 5'-UAAGUGCUUC CAUGUUU-3' (SEQ.ID.NO.7) in the 5'-end, and further in conjunction with the use of some wound-healing-related defined factors, including but not limited to basic fibroblast growth factor (bFGF)/fibroblast growth factor 2 (FGF-2), leukemia inhibitory factor (LIF), insulin-like growth factor (IGF), Epidermal growth factor (EGF), platelet-derived growth factor (PDGF), vascular endothelial growth factor (VEGF), transforming growth factor (TGF), tumor necrosis factor (TNF), stem cell factor (SCF), homeobox proteins (HOX), Notch, GSK, Wnt/beta-Catenin signals, interleukins, and/or bone morphogenetic proteins (BMPs). The resulting amplified ASCs are useful for treating a variety of human aging- and cell dysfunction-associated disorders, including but not limited to Alzheimer's disease, Parkinson's disease, motor neuron disease, stroke, diabetes, osteoporosis, myocardial infraction, hemophilia, anemia, AIDS, leukemia, lymphoma and many kinds of cancers as well as aging.

In principle, the present invention is related to a novel mechanism of inducible symmetric ASC division recently found in a skin wound healing model in vivo (U.S. Pat. No. 9,879,263 and U.S. patent application Ser. No. 15/661,346 to Lin). However, our previous inventions did not reveal any of the defined factors required for being used with miR-302 in order to induce ASC expansion in vitro. To overcome this problem, the present invention further teaches all the required and optional defined factors that are involved in the mechanism of induced ASC expansion in vitro.

BRIEF DESCRIPTION OF THE DRAWINGS

The patent or application file contains at least one color drawing. Copies of this patent or patent application publication with color drawing will be provided by the USPTO upon request and payment of the necessary fee.

Referring particularly to the drawings for the purpose of illustration only and not limitation, there is illustrated.

EXAMPLES

Figure 1:
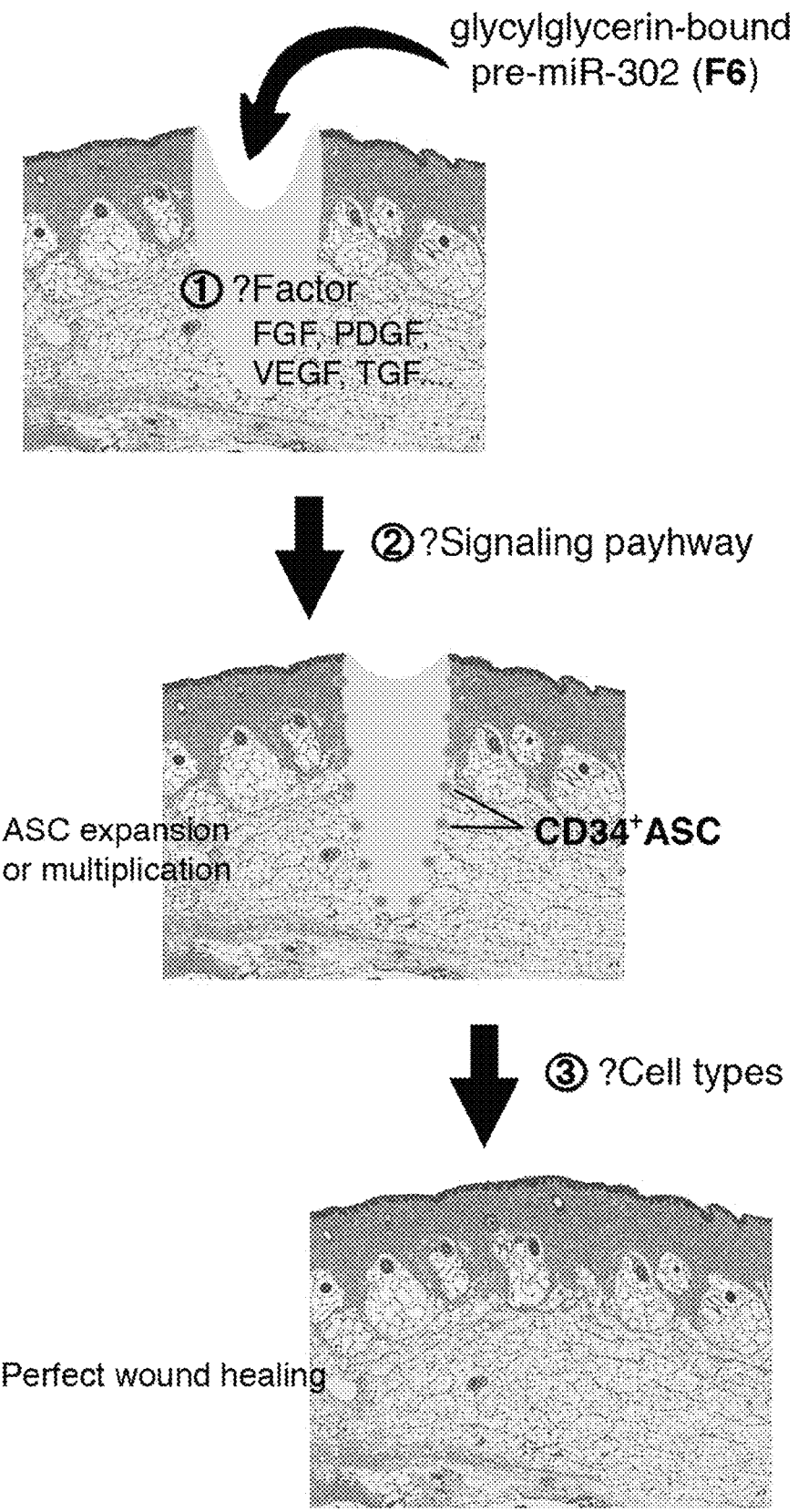
FIG. 1 shows the proposed model of the miR-302-mediated perfect (scar-less) wound healing mechanism in vivo.
Figure 2:
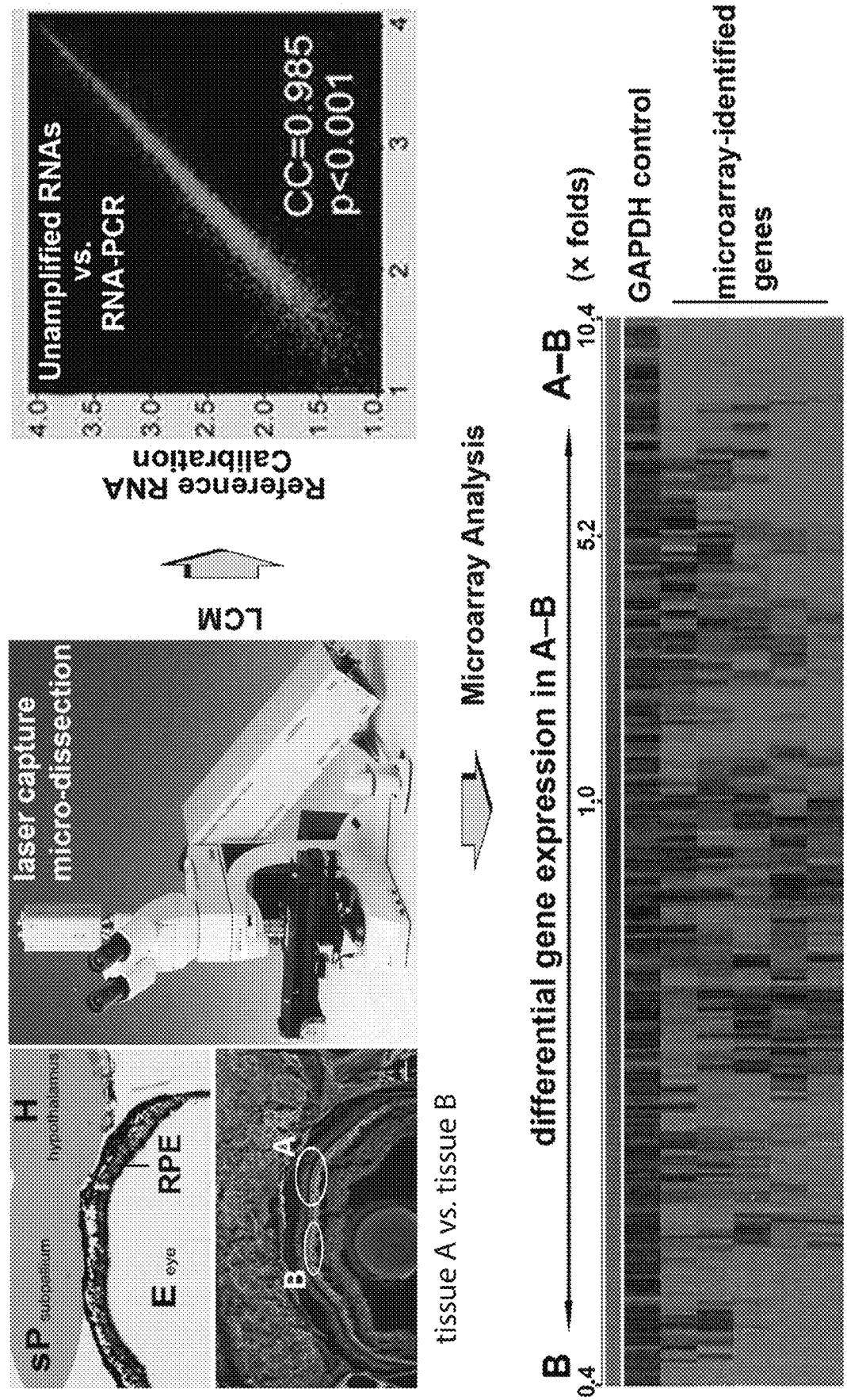
FIG. 2 shows the technology of LCM-microarray analyses to find differentially expressed genes between two different tissue samples isolated in vivo. For example, two different types of tissue cells obtained from different sample regions can be collected, using a laser capture microdissection machine (LCM). After that, individual mRNA/cDNA libraries are separately amplified and collected from each of these LCM-dissected tissue cell samples and then further used for microarray analysis, respectively. Using this LCM-microarray approach, we have studied and compared the differential gene expression patterns between the isolated CD34$^+$ASCs in vivo and the induced iCD34$^+$ASCs in vitro as well as other non-ASC tissue cells.
Figure 3:
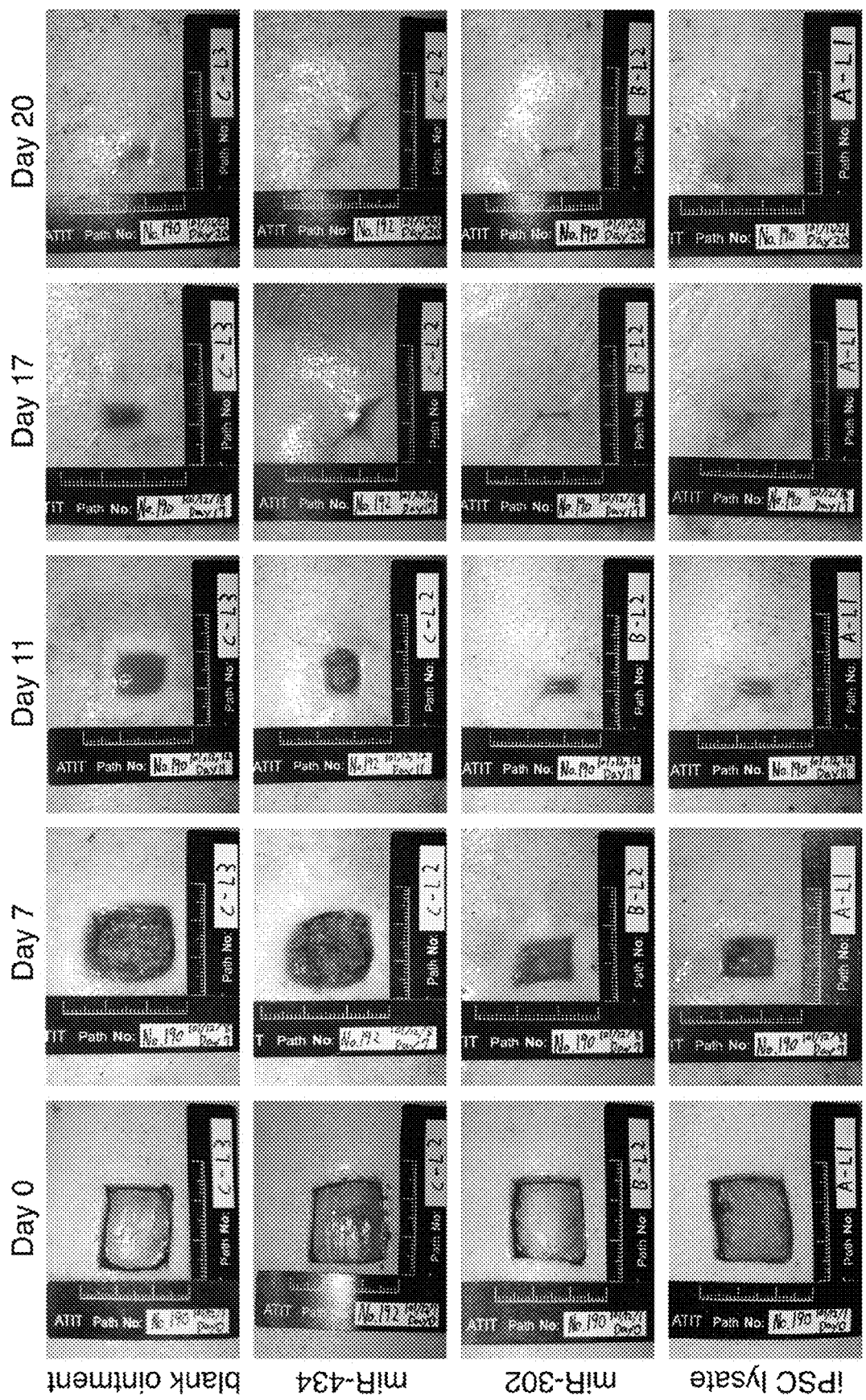
FIG. 3 shows the comparison of in-vivo wound healing rates among treatments of antibiotic ointment only (top), antibiotic ointment with 1 mg/mL of miR-434-mimic siRNAs (2nd line), antibiotic ointment with 1 mg/mL of isolated miR-302 precursors (3rd line), and antibiotic ointment with 5 mg/mL of isolated iPSC lysate (bottom line). Sample number size is n=12 for the miR-302 and iPSC lysate treatment groups, respectively, while n=6 for the blank control (ointment only) and miR-434 treatment groups, respectively.
Figure 4:
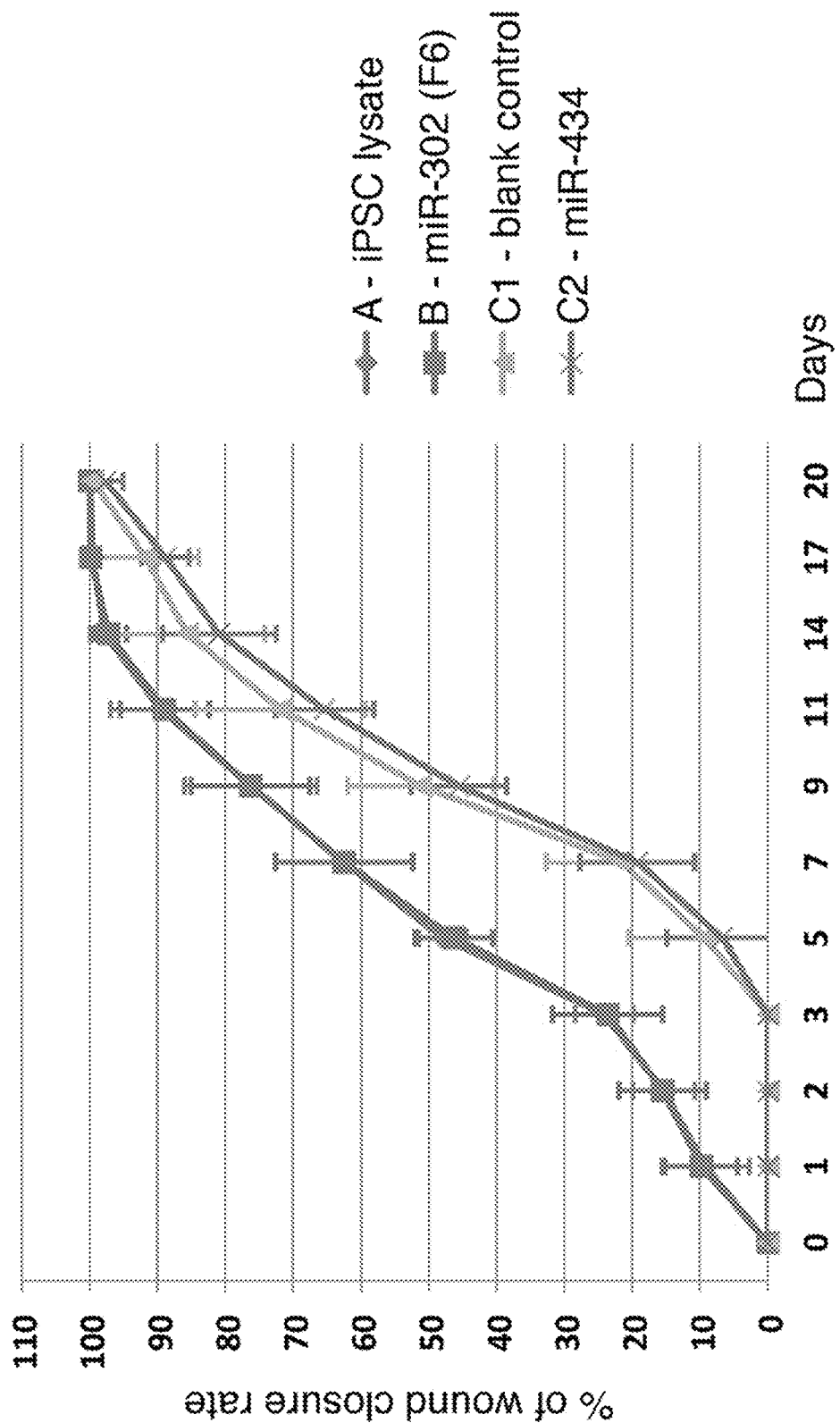
FIG. 4 shows the time-course results of wound closure rates (%) after treatments of (A) iPSC lysate (blue diamond), (B) miR-302 precursors (miR-302; red square), (C1) antibiotic ointment only (blank control; green triangle), and (C2) miR-434-mimic siRNA (purple cross). The results demonstrate that both of the iPSC lysate and miR-302 treatments can significantly increase fast wound healing rates in vivo (p<0.01), while other controls can not.
Figure 5:
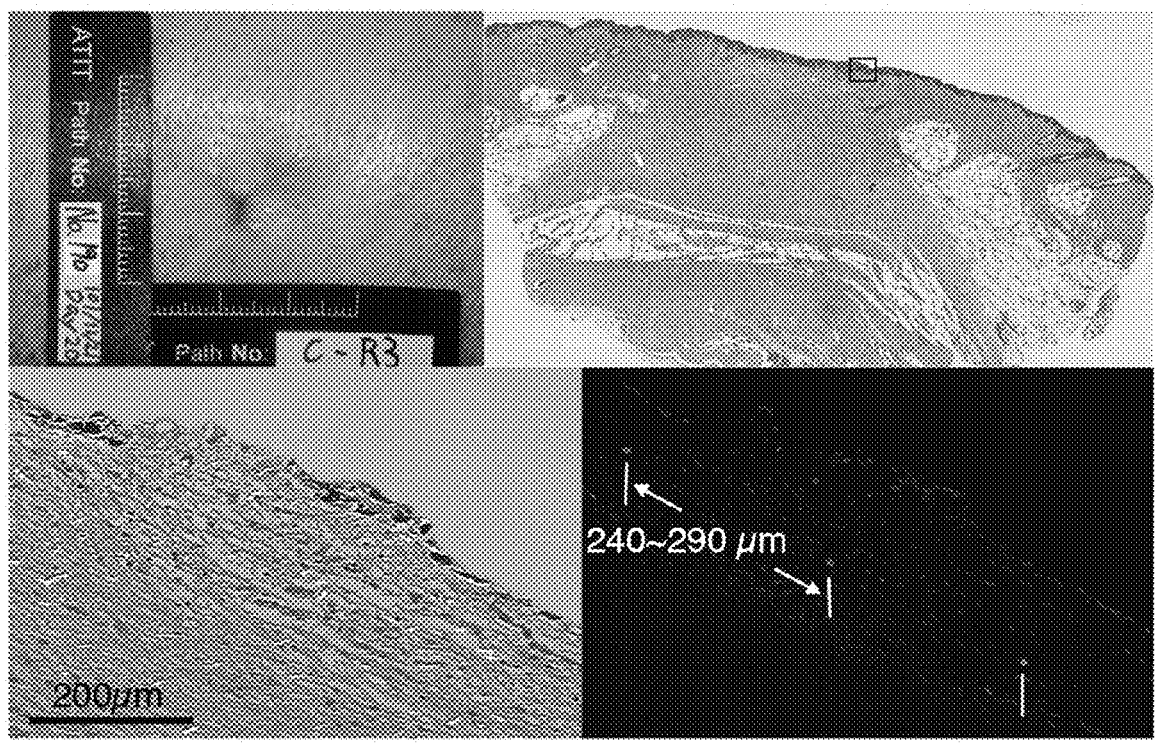
FIG. 5 shows the comparison of wound healing results between untreated (top; 190-CR3) and miR-302-treated (bottom; 190-BR2) skin samples in vivo. The isolated pre-miR-302 (20~1000 pg/mL) were formulated with antibiotic ointment and directly applied to 2 cm×2 cm open wounds on pig back skins in vivo. Approximately 2~3-week after treatments, a part of the healed wound samples were dissected and further made into tissue sections for histological examination. The results showed that no or very little scar (scar-less) could be found in the miR-302-treated samples (perfect healing rate n=6/6), whereas almost all untreated (treated with only antibiotic ointment) wounds formed large scars. Noteworthily, a significantly high amount (≥40~1000 fold higher) of CD34-positive adult stem cell clusters (CD34$^+$ASCs labeled by green fluorescent antibodies) were found in the miR-302-treated samples (n=6/6), compared to that of the untreated control wounds. These results indicate that miR-302 can function to induce CD34$^+$ASC expansion and derivation, so as to enhance tissue repairing and regeneration, leading to a very beneficial therapeutic effect on lesions caused by human degenerative diseases (HDD).
Figure 5:
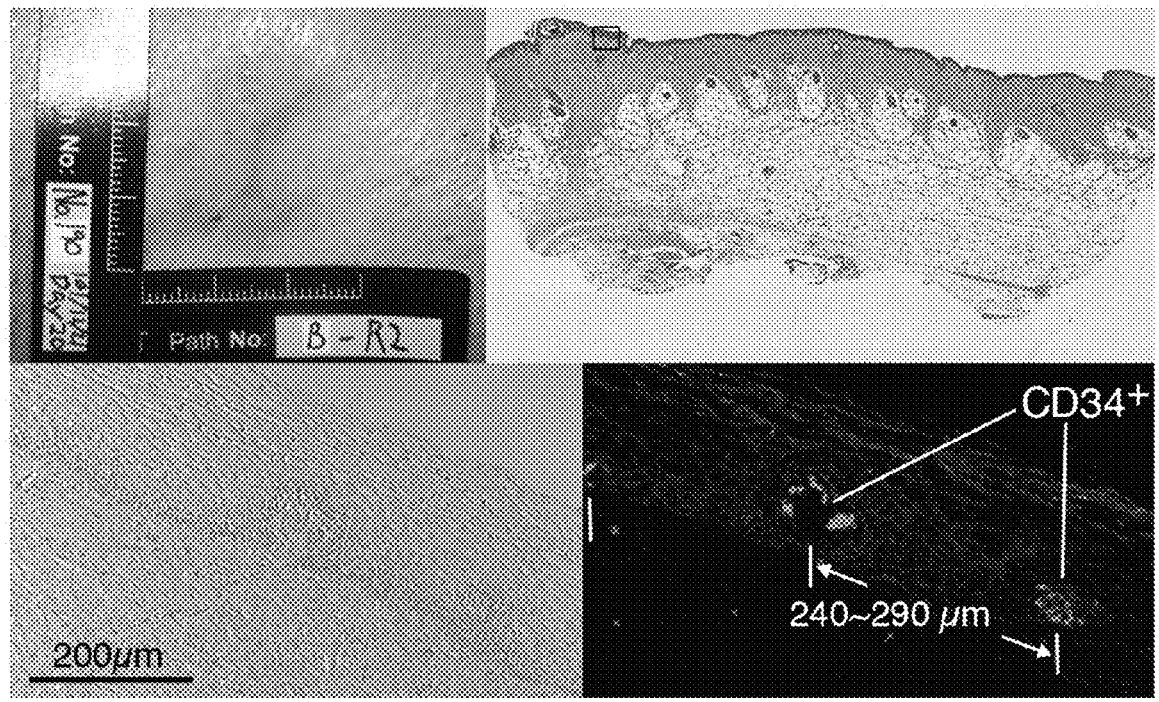
Figure 6:
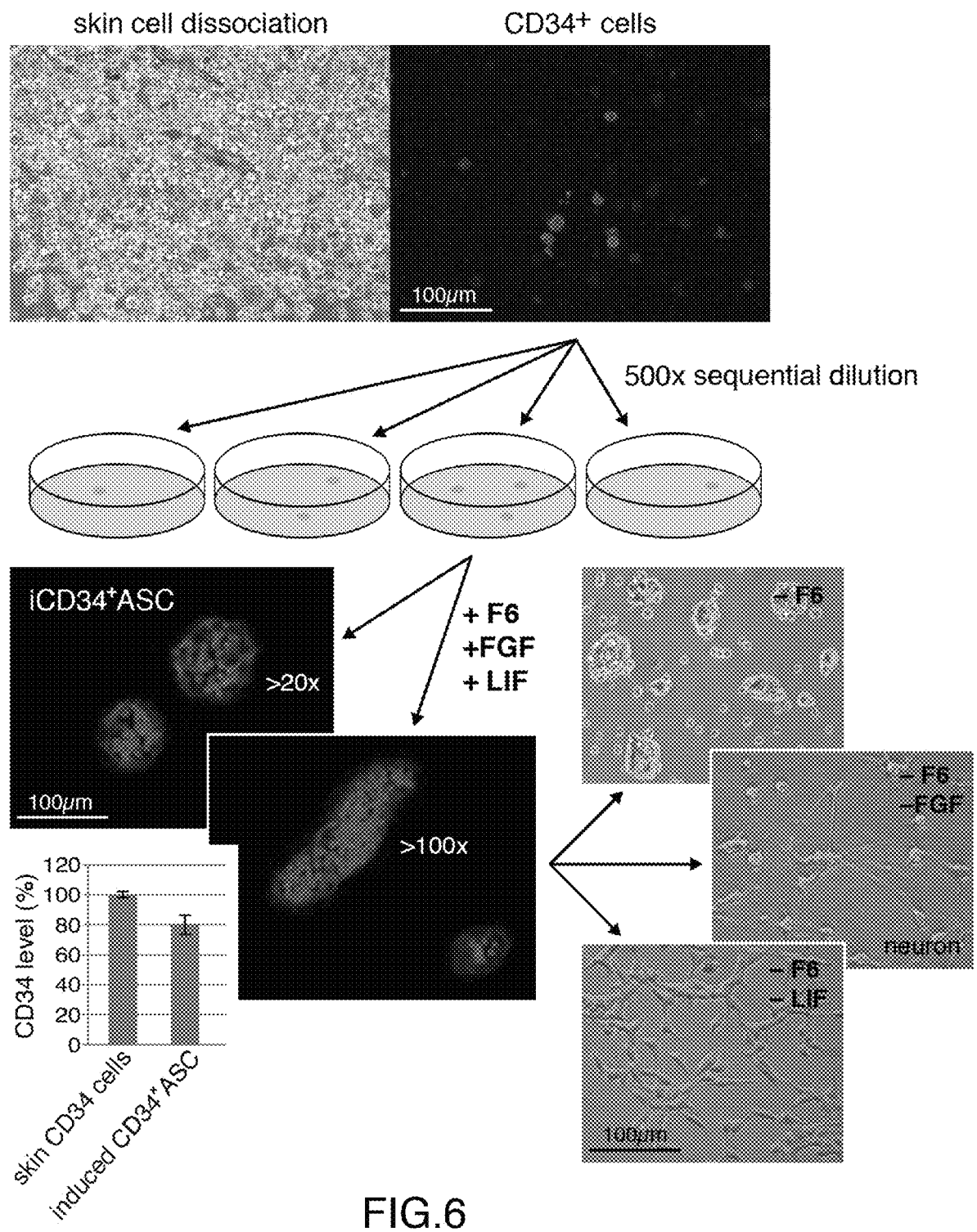
FIG. 6 shows the results of induced CD34$^+$ASC expansion and derivation in vitro. After skin cell dissociation and further sequential dilution to acquire single cell colonies, CD34$^+$ASCs were identified using fluorescent immunocytochemical staining with anti-CD34 antibody (top panels; green). These isolated CD34$^+$ASCs can be further repeatedly cultivated and amplified in vitro in an established culture condition containing miR-302 and the identified defined factors (such as bFGF/FGF2, LIF, and some other optional wound healing related factors) (bottom left pictures). The amplified CDWASCs (called iCDWASCs) so obtained can be further differentiated into several different tissue cell types in the skin- and neuro-ectoderm lineage (bottom right pictures). (n=25,p<0.001).
Figure 7:
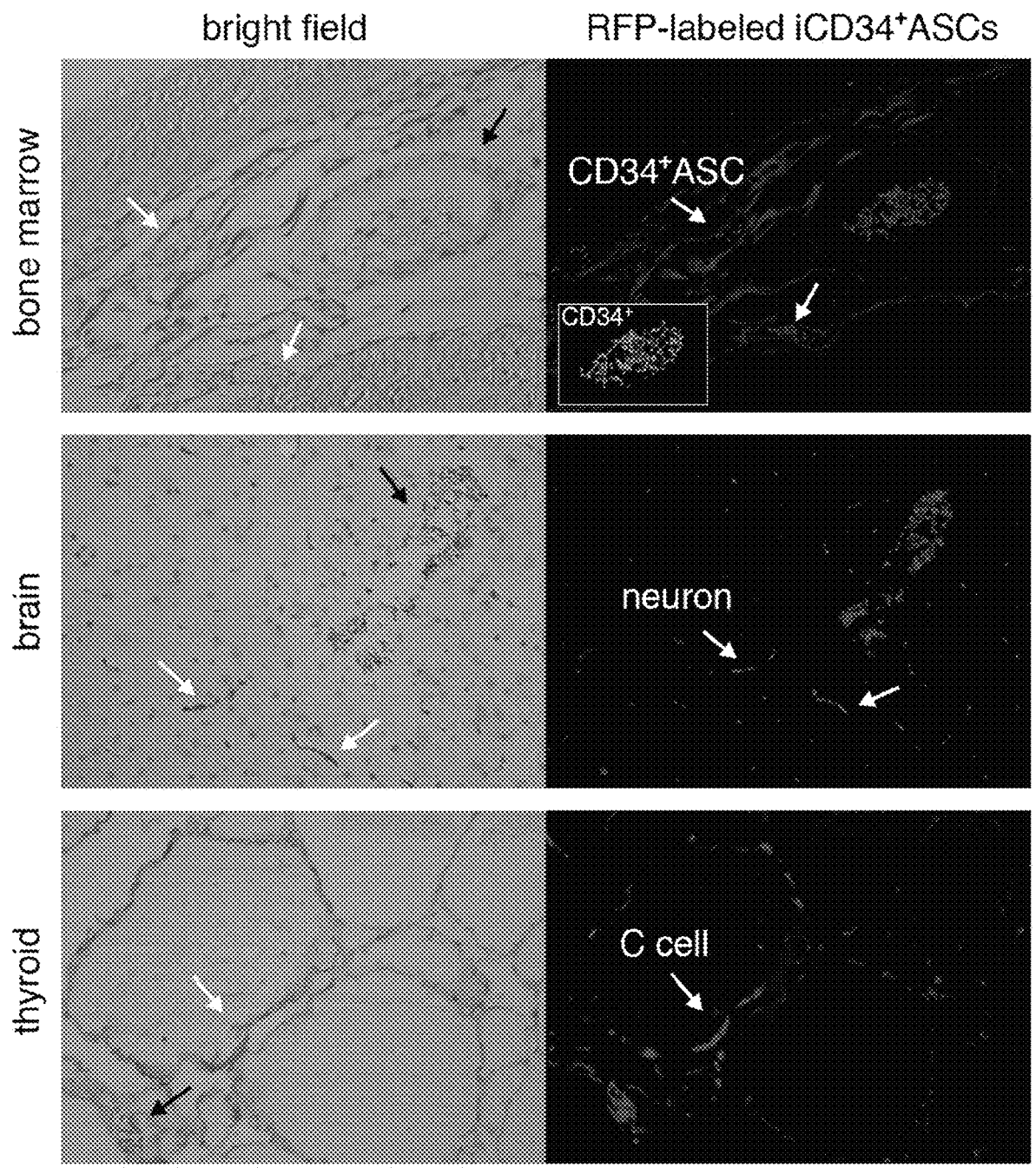
FIG. 7 shows the transplantation results of iCD34$^+$ASCs into NOD-SCID mice in vivo (n=3). Each mouse was implanted with 5×10$^5$ iCD34$^+$ASCs through tail vein injection. All iCD34$^+$ASCs were labeled with a red fluorescent protein (RFP) transfectively delivered by a pLVX-EF1alpha-HcRed-N1 lentiviral vector. Approximately 3 weeks after transplantation, all major organs and tissues were separately collected and made into tissue section slides, and then used for IHC staining and microscopic examination to identify the implanted iCD34$^+$ASC expansion pouches and the iCDWASC-differentiated tissue cells (all labeled in red) in vivo. Although three major differentiated tissue types were shown here, the iCDWASC-differentiated tissue cell types found in most up-to-day results include but not limited to bone marrow, brain, heart, lung, spleen, thyroid, kidney, and liver, most of which are derived from either the ectoderm or mesoderm but rarely from endoderm lineage.

In the experimental disclosure which follows, the following abbreviations apply: M (molar); mM (millimolar); μm (micromolar); mol (moles); pmol (picomoles); gm (grams); mg (milligrams) μg (micrograms); ng (nanograms); L (liters); ml (milliliters); μl (microliters); ° C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecyl sulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

1. CD34$^+$ASC Isolation, Cultivation and Expansion in Vitro

The starting CD34$^+$ASCs can be obtained from either hair follicles following our protocol (Lin et al., 2011), or enzymatically dissociated skin cells using Aasen's protocol (*Nat. Protocols* 5, 371-382, 2010), or simply from the buffy coat fraction of heparin-treated peripheral blood cells. The tissue samples must be kept fresh and immediately treated by a mixture of 4 mg/mL collagenase I and 0.25% TrypLE for 15-45 min, depending on cell density, and rinsed by HBSS containing trypsin inhibitor two times and then transferred to a new sterilized microtube containing 0.3 mL of feeder-free MSC Expansion SFM culture medium (ASC culture medium; IrvineScientific, CA). After that, cells were further dissociated by shaking in a microtube incubator for 1 min at 37° C. and then transferred the whole 0.3 mL cell suspension to a 35-mm Matrigel-coated culture dish containing 1 mL of feeder-free MSC Expansion SFM culture medium supplemented with formulated miR-302/pre-miR-302, LIF, and bFGF/FGF2, or other optional defined factors. The used concentration of miR-302/pre-miR-302, LIF, bFGF/FGF2, and other optional defined factors is ranged from 0.001 microgram/mL to 500 microgram/mL (0.001~500 μg/mL), respectively; most preferably, the used concentration is ranged from 10~200 microgram/mL (10~200 μg/mL) for miR-302/pre-miR-302 and 2~20 nanogram/mL (2~20 ng/mL) for LIF, bFGF/FGF2, and/or other optional defined factors, respectively, in the ASC culture medium. The ASC culture medium and all the supplements must be refreshed every 3∞4 days. The CD34⁺ASCs were grown into many pouch-like expansion colonies and could be separately collected and further passaged at about 50%-60% confluence by exposing the cells to TrypLE for 1 min and then rinsing two times in HBSS containing trypsin inhibitor. For more ASC expansion, the detached CD34⁺ASCs were replated at 1:5~1:500 dilution in fresh ASC culture medium supplemented with formulated pre-miR-302, LIF, bFGF/FGF2, and/or other optional defined factors.

2. MicroRNA and Pre-miRNA Isolation and Preparation

Native miR-302 and pre-miR-302 can be extracted from the cytosol of either hESCs or iPSCs, or both, following Lin SL's protocol (Lin SL, 2018). For collecting cytosol, ESCs or iPSCs were broken by ultracentrifugation at 17,500 g for 30 min at 4° C. and further filtered by passing the suspension through a 0.01 micron ultrafilter column (30 kDa/100 nucleotide-cutoff; Amicon Ultra-0.5 30K), following the manufacturer's suggestions (Millipore, Billerica, Mass.). Approximately 0.8~1 mL of ESC or iPSC cytosol could be recovered from 1~1.2 billion ESCs or iPSCs, respectively. For extracting miR-302 and pre-miR-302, the ESC or iPSC cytosol was further purified by a 0.001 micron nanofilter column (3 kDa/10 nucleotide-cutoff; Amicon Ultra-0.5 3K) and recovered in the flow-through portion, while all small RNAs were collected on the nanofilter and then dissolved in double-autoclaved DEPC-treated $ddH_2O$ (pH 5.5~5.6) for further purification using high performance liquid chromatography (HPLC). The sizes of small RNAs so obtained were ranged from about 10 to 110 nucleotides (or 3~30 kDa), including pre-miRNAs/miRNAs and a few tRNAs. Using miRNA microarray analysis, we have confirmed that over 90% of the isolated small RNAs are pre-miR-302 and miR-302, which are the most abundant and stable small RNAs in ESCs and iPSCs. Alternatively, synthetic miR-302-mimic siRNA and/or shRNA may be used in place of native miRNAs/pre-miRNAs. Furthermore, bacterial competent cells may be used to replace ESCs and iPSCs for miR-302/pre-miR-302 production and extraction.

3. miRNA Microarray and RT-qPCR Analyses

The purity and quantity of isolated small RNAs were first assessed with 2%~3% low-melting-point agarose gel electrophoresis and spectrophotometer at UV 260nm/280nm (Bio-Rad, Hercules, Calif.). Then, microarray analyses were performed by LC Sciences (San Diego, Calif.), using approximately 10 μg of the small RNAs isolated from each sample, respectively. Each microarray chip was hybridized with a single sample labeled with either Cy3 or Cy5 dye. Background subtraction, data normalization and statistic calculation were performed following manufacturer's protocols. For a dual sample assay, a p-value calculation was performed and a list of differentially expressed transcripts more than 3-fold (yellow-red signals) was produced. For RT-qPCR, we used a set of TaqMan primers directed against hsa-miR-302a and the related Real-Time PCR kit (Life Technologies, Grand Island, N.Y.), following the manufacturer's instructions. Signals were detected with an ABI7300 Real-Time PCR System (Applied Biosystems, Life Technologies).

4. Immunostaining Assay

Embedding, sectioning and immunostaining tissue samples were performed as previously reported (Lin et al., 2008 and 2010). Primary antibodies include green fluorescent dye-labeled anti-CD34 (Santa Cruz and Sigma). Alternatively, fluorescent dye-labeled goat anti-rabbit or horse anti-mouse antibody was used as the secondary antibody (Invitrogen-Molecular Probes, Carlsbad, Calif.). Positive results were examined and analyzed at 100× or 200× magnification under a fluorescent 80i microscopic quantitation system with a Metamorph imaging program (Nikon).

5. Bisulfite DNA Sequencing

Genomic DNAs were isolated from 2,000,000 cells using a DNA isolation kit (Roche) and 1 μg of the isolated DNAs was further treated with bisulfite (CpGenome DNA modification kit, Chemicon, Temecula, Calif.), following the manufacturers' suggestion. The bisulfite treatment converted all unmethylated cytosine to uracil, while methylated cytosine remained as cytosine. For bisulfite DNA sequencing, we amplified the promoter region of the Oct4 gene with PCR primers: 5'-GAGGCTGGAG CAGAAGGATT GCTTTGG-3' (SEQ.ID.NO.12) and 5'-CCCTCCTGAC CCATCACCTC CACCACC-3' (SEQ.ID.NO.13). For PCR, the bisulfite-modified DNAs (50 ng) were mixed with the primers (total 100 pmol) in 1× PCR buffer, heated to 94° C. for 2 min, and immediately cooled on ice. Next, 25 cycles of PCR were performed as follows: 94° C. for 1 min and 70° C. for 3 min, using an Expand High Fidelity PCR kit (Roche). The PCR product with a correct size was further fractionized by 3% agarose gel electrophoresis, purified by a gel extraction filter (Qiagen), and then used in DNA sequencing. After that, a detailed profile of DNA methylation sites was generated by comparing the unchanged cytosine in the converted DNA sequence to the unconverted one.

6. Flow Cytometry

Cells were trypsinized, pelleted and fixed by re-suspension in 1 ml of pre-chilled 70% methanol in PBS for 1 hour at −20° C. The cells were pelleted and washed once with 1 ml of PBS and then pelleted again and resuspended in 1 ml of 1 mg/ml propidium iodide, 0.5 μg/ml RNase in PBS for 30 min at 37° C. After that, about 15,000 cells were analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm.

7. Skin Wound Healing Model and CD34⁺ASC Expansion in Vivo

The Landrace is a white, lop-eared pig breed found in most Central and Eastern European countries. The male Landrace Pigs used for establishing the skin wound models were provided and cared for by ATIT overseen by specially-assigned personnel and qualified veterinarians. Under their supervision, these animals were provided with adequate care in accordance with the Animal Welfare Act in Taiwan. These pigs average 3 months of age and weigh between 18 to 23 kg each. All animals were euthanized at the end of the study.

The animals were anesthetized using Zoletil 50 (6 mg/kg) and their backs were subsequently shaved. Six (6) full-thickness square wounds (2cm×2cm or 4 $cm^2$ each) were generated using a sterilized surgical scalpel, with 3 wounds each on the right and left side of each animal. Each wound was received topical treatment with 0.5 mL of antibiotic ointment containing either (A) iPSC lysate (5 mg/mL), (B) formulated miR-302 precursors (1 mg/mL), (C1) blank, or (C2) miR-434 siRNA (1 mg/mL), respectively. The treatments were applied on days 0, 1, 2, 3, 4, 5, 7, 9, 11, 14 and 17. Photos of each wound were taken with Sony DSC-H9 camera on days 0, 1, 2, 3, 4, 5, 7, 9, 11, 14, 17 and 20. The area of each wound at each time point was determined using the Image Pro Plus 7.0 imaging software. Percentage of wound healing or closure at each treatment time point was calculated according to the formula: (day 0 wound area−day N wound area)/day 0 wound area×100. Also, tissue samples were collected from each wound and soaked in 10% (v/v) formalin solution before being used for preparing histological sections for H&E staining.

8. Statistic Analysis

All data were shown as averages and standard deviations (SD). Mean of each test group was calculated by AVERAGE of Microsoft Excel. SD was performed by STDEV. Statistical analysis of data was performed by One-Way ANOVA. Tukey and Dunnett's t post hoc test were used to identify the significance of data difference in each group. $p<0.05$ was considered significant (SPSS v12.0, Claritas Inc).

REFERENCES

1. Aasen et al., (2010) Isolation and cultivation of human keratinocytes from skin or plucked hair for the generation of induced pluripotent stem cells. *Nature Protocols* 5, 371-382.
2. Chen S K J and Lin S L. (2013) Recent patents on microRNA-induced pluripotent stem cell generation. *Recent Patents on Regenerative Medicine* 3:5-16.
3. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
4. Lin S L and Ying S Y. (2008) Role of mir-302 microRNA family in stem cell pluripotency and renewal. Ying S Y. (Ed.) *Current Perspectives in MicroRNAs*. Springer Publishers press, New York, pp 167-185.
5. Lin S L, Chang D, Ying S Y, Leu D and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.
6. Lin S L, Chang D, Lin C H, Ying S Y, Leu D and Wu D T S. (2011) Regulation of somatic cell reprogramming through inducible mir-302 expression. *Nucleic Acids Res.* 39, 1054-1065.
7. Lin S L and Ying S Y. (2013) Mechanism and method for generating tumor-free iPS cells using intronic microRNA miR-302 induction. *Methods Mol Biol.* 936, 295-312.
8. Lin S L. (2018) Identification and Isolation of Novel Sugar-Like RNA Protecting Materials: Glycylglycerins from Pluripotent Stem Cells. *Methods Mol Biol.* 1733, 305-316.
9. Simonsson S and Gurdon J. (2004) DNA demethylation is necessary for the epigenetic reprogramming of somatic cell nuclei. *Nat Cell Biol.* 6, 984-990.
10. Takahashi et al. (2006) Induction of pluripotent stem cells from mouse embryonic and adult fibroblast cultures by defined factors. *Cell* 126, 663-676.
11. Wang et al. (2008) Embryonic stem cell-specific microRNAs regulate the G1-S transition and promote rapid proliferation. *Nat. Genet.* 40, 1478-1483.
12. Wernig et al. (2007) In vitro reprogramming of fibroblasts into a pluripotent ES-cell-like state. *Nature* 448, 318-324.
13. Xu R H, Peck R M, Li D S, Feng X, Ludwig T and Thomson J A. (2005) Basic FGF and suppression of BMP signaling sustain undifferentiated proliferation of human ES cells. *Nat Methods.* 2, 185-190.
14. Ying Q L, Nichols J, Chambers I and Smith A. (2003) BMP induction of Id proteins suppresses differentiation and sustains embryonic stem cell self-renewal in collaboration with STAT. *Cell* 115, 281-292.
15. Ying S Y, Fang W and Lin S L. (2018) The miR-302-mediated induction of pluripotent stem cells (iPSCs): Multiple synergistic reprogramming mechanisms. *Methods Mol. Biol.* 1733, 283-304.
16. Yu et al. (2007). Induced pluripotent stem cell lines derived from human somatic cells. *Science* 318, 1917-1920.
17. European Patent No. EP 2198025 to Lin.
18. U.S. Pat. No. 9,387,251 to Lin.
19. U.S. Pat. No. 9,394,538 to Lin.
20. U.S. Pat. No. 9,422,559 to Lin.
21. U.S. Pat. No. 9,567,591 to Lin.
22. U.S. Pat. No. 9.879,263 to Lin.
23. U.S. patent application Ser. No. 12/318,806 to Lin.
24. U.S. patent application Ser. No. 13/572,263 to Lin.

```
                        SEQUENCE LISTING (1)     GENERAL INFORMATION:
        (iii)   NUMBER OF SEQUENCES: 13

(2)     INFORMATION FOR SEQ ID NO: 1:
        (i)     SEQUENCE CHARACTERISTICS:
                (A) LENGTH: 69 base pairs
                (B) TYPE: nucleic acid
                (C) STRANDEDNESS: single
                (D) TOPOLOGY: hairpin (ii)    MOLECULE TYPE: RNA
                (A) DESCRIPTION: /desc = "natural" or "synthetic"

(iii)   HYPOTHETICAL: NO (iv)    ANTI-SENSE: NO (xi)    SEQUENCE DESCRIPTION: SEQ ID NO: 1:
                CCACCACUUA AACGUGGAUG UACUUGCUUU GAAACUAAAG              69
                AAGUAAGUGC UUCCAUGUUU UGGUGAUGG
```

```
                         SEQUENCE LISTING (3)  INFORMATION FOR SEQ ID NO: 2:
     (i)    SEQUENCE CHARACTERISTICS:
            (A) LENGTH: 73 base pairs
            (B) TYPE: nucleic acid
            (C) STRANDEDNESS: single
            (D) TOPOLOGY: hairpin (ii)   MOLECULE TYPE: RNA
            (A) DESCRIPTION: /desc = "natural" or "synthetic"

(iii)  HYPOTHETICAL: NO (iv)   ANTI-SENSE: NO (xi)   SEQUENCE DESCRIPTION: SEQ ID NO: 2:
            GCUCCCUUCA ACUUUAACAU GGAAGUGCUU UCUGUGACUU          73
            UAAAAGUAAGU GCUUCCAUGU UUUAGUAGG AGU (4)  INFORMATION FOR SEQ ID NO: 3:
     (i)    SEQUENCE CHARACTERISTICS:
            (A) LENGTH: 68 base pairs
            (B) TYPE: nucleic acid
            (C) STRANDEDNESS: single
            (D) TOPOLOGY: hairpin (ii)   MOLECULE TYPE: RNA
            (A) DESCRIPTION: /desc = "natural" or "synthetic"

(iii)  HYPOTHETICAL: NO (iv)   ANTI-SENSE: NO (xi)   SEQUENCE DESCRIPTION: SEQ ID NO: 3:
            CCUUUGCUUU AACAUGGGGG UACCUGCUGU GUGAAACAAA          68
            AGUAAGUGCU UCCAUGUUUC AGUGGAGG (5)  INFORMATION FOR SEQ ID NO: 4:
     (i)    SEQUENCE CHARACTERISTICS:
            (A) LENGTH: 68 base pairs
            (B) TYPE: nucleic acid
            (C) STRANDEDNESS: single
            (D) TOPOLOGY: hairpin (ii)   MOLECULE TYPE: RNA
            (A) DESCRIPTION: /desc = "natural" or "synthetic"

(iii)  HYPOTHETICAL: NO (iv)   ANTI-SENSE: NO (xi)   SEQUENCE DESCRIPTION: SEQ ID NO: 4:
            CCUCUACUUU AACAUGGAGG CACUUGCUGU GACAUGACAA          68
            AAAUAAGUGC UUCCAUGUUU GAGUGUGG (6)  INFORMATION FOR SEQ ID NO: 5:
     (i)    SEQUENCE CHARACTERISTICS:
            (A) LENGTH: 23 base pairs
            (B) TYPE: nucleic acid
            (C) STRANDEDNESS: single
            (D) TOPOLOGY: linear (ii)   MOLECULE TYPE: RNA
            (A) DESCRIPTION: /desc = "synthetic"

(iii)  HYPOTHETICAL: NO (iv)   ANTI-SENSE: YES (xi)   SEQUENCE DESCRIPTION: SEQ ID NO: 5:
            UCACCAAAAC AUGGAAGCAC UUA                            23
```

```
                         SEQUENCE LISTING (7)  INFORMATION FOR SEQ ID NO: 6:
     (i)    SEQUENCE CHARACTERISTICS:
            (A) LENGTH: 23 base pairs
            (B) TYPE: nucleic acid
            (C) STRANDEDNESS: single
            (D) TOPOLOGY: linear (ii)   MOLECULE TYPE: RNA
            (A) DESCRIPTION: /desc = "natural"

(iii)  HYPOTHETICAL: NO (iv)   ANTI-SENSE: YES (xi)   SEQUENCE DESCRIPTION: SEQ ID NO: 6:
            ACUUAAACGU GGAUGUACUU GCU                             23

(8)  INFORMATION FOR SEQ ID NO: 7:
     (i)    SEQUENCE CHARACTERISTICS:
            (A) LENGTH: 17 base pairs
            (B) TYPE: nucleic acid
            (C) STRANDEDNESS: single
            (D) TOPOLOGY: linear (ii)   MOLECULE TYPE: RNA
            (A) DESCRIPTION: /desc = "natural" or "synthetic"

(iii)  HYPOTHETICAL: NO (iv)   ANTI-SENSE: NO (xi)   SEQUENCE DESCRIPTION: SEQ ID NO: 7:
            UAAGUGCUUC CAUGUUU                                    17

(9)  INFORMATION FOR SEQ ID NO: 8:
     (i)    SEQUENCE CHARACTERISTICS:
            (A) LENGTH: 23 base pairs
            (B) TYPE: nucleic acid
            (C) STRANDEDNESS: single
            (D) TOPOLOGY: linear (ii)   MOLECULE TYPE: RNA
            (A) DESCRIPTION: /desc = "natural"

(iii)  HYPOTHETICAL: NO (iv)   ANTI-SENSE: NO (xi)   SEQUENCE DESCRIPTION: SEQ ID NO: 8:
            UAAGUGCUUC CAUGUUUUGG UGA                             23

(10) INFORMATION FOR SEQ ID NO: 9:
     (i)    SEQUENCE CHARACTERISTICS:
            (A) LENGTH: 23 base pairs
            (B) TYPE: nucleic acid
            (C) STRANDEDNESS: single
            (D) TOPOLOGY: linear (ii)   MOLECULE TYPE: RNA
            (A) DESCRIPTION: /desc = "natural"

(iii)  HYPOTHETICAL: NO (iv)   ANTI-SENSE: NO (xi)   SEQUENCE DESCRIPTION: SEQ ID NO: 9:
            UAAGUGCUUC CAUGUUUUAG UAG                             23

(11) INFORMATION FOR SEQ ID NO: 10:
     (i)    SEQUENCE CHARACTERISTICS:
            (A) LENGTH: 23 base pairs
            (B) TYPE: nucleic acid
            (C) STRANDEDNESS: single
            (D) TOPOLOGY: linear
```

```
                            SEQUENCE LISTING (ii)  MOLECULE TYPE: RNA
              (A) DESCRIPTION: /desc = "natural"

(iii) HYPOTHETICAL: NO (iv)  ANTI-SENSE: NO (xi)  SEQUENCE DESCRIPTION: SEQ ID NO: 11:
              UAAGUGCUUC CAUGUUUCAG UGG                              23

(12) INFORMATION FOR SEQ ID NO: 10:
     (i)   SEQUENCE CHARACTERISTICS:
           (A) LENGTH: 23 base pairs
           (B) TYPE: nucleic acid
           (C) STRANDEDNESS: single
           (D) TOPOLOGY: linear (ii)  MOLECULE TYPE: RNA
              (A) DESCRIPTION: /desc = "natural"

(iii) HYPOTHETICAL: NO (iv)  ANTI-SENSE: NO (xi)  SEQUENCE DESCRIPTION: SEQ ID NO: 11:
              UAAGUGCUUC CAUGUUUGAG UGU                              23

(13) INFORMATION FOR SEQ ID NO: 12:
     (i)   SEQUENCE CHARACTERISTICS:
           (A) LENGTH: 27 base pairs
           (B) TYPE: nucleic acid
           (C) STRANDEDNESS: single
           (D) TOPOLOGY: linear (ii)  MOLECULE TYPE: other nucleic acids
              (A) DESCRIPTION: /desc = "synthetic"

(iii) HYPOTHETICAL: YES (iv)  ANTI-SENSE: YES (xi)  SEQUENCE DESCRIPTION: SEQ ID NO: 12:
              GAGGCTGGAG CAGAAGGATT GCTTTGG                          27

(14) INFORMATION FOR SEQ ID NO: 13:
     (i)   SEQUENCE CHARACTERISTICS:
           (A) LENGTH: 27 base pairs
           (B) TYPE: nucleic acid
           (C) STRANDEDNESS: single
           (D) TOPOLOGY: linear (ii)  MOLECULE TYPE: other nucleic acids
              (A)  DESCRIPTION: /desc = "synthetic"

(iii) HYPOTHETICAL: YES (iv)  ANTI-SENSE: YES (xi)  SEQUENCE DESCRIPTION: SEQ ID NO: 13:
              CCCTCCTGAC CCATCACCTC CACCACC                          27
```

```
                            SEQUENCE LISTING

<160> NUMBER OF SEQ ID NOS: 13

<210> SEQ ID NO 1
<211> LENGTH: 69
<212> TYPE: RNA
<213> ORGANISM: Artificial Sequence
<220> FEATURE:
<223> OTHER INFORMATION: Synthetic
```

```
<400> SEQUENCE: 1
ccaccacuua aacguggaug uacuugcuuu gaaacuaaag aaguaagugc uuccauguuu    60
uggugaugg                                                           69

<210> SEQ ID NO 2
<211> LENGTH: 73
<212> TYPE: RNA
<213> ORGANISM: Artificial Sequence
<220> FEATURE:
<223> OTHER INFORMATION: Synthetic

<400> SEQUENCE: 2
gcucccuuca acuuuaacau ggaagugcuu ucgugacuu uaaaaguaag ugcuuccaug     60
uuuuaguagg agu                                                      73

<210> SEQ ID NO 3
<211> LENGTH: 68
<212> TYPE: RNA
<213> ORGANISM: Artificial Sequence
<220> FEATURE:
<223> OTHER INFORMATION: Synthetic

<400> SEQUENCE: 3
ccuuugcuuu aacauggggg uaccugcugu gugaaacaaa aguaagugcu uccauguuc     60 aguggagg                                                            68

<210> SEQ ID NO 4
<211> LENGTH: 68
<212> TYPE: RNA
<213> ORGANISM: Artificial Sequence
<220> FEATURE:
<223> OTHER INFORMATION: Synthetic

<400> SEQUENCE: 4
ccucuacuuu aacauggagg cacuugcugu gacaugacaa aaauaagugc uuccauguuu    60
gagugugg                                                            68

<210> SEQ ID NO 5
<211> LENGTH: 23
<212> TYPE: RNA
<213> ORGANISM: Artificial Sequence
<220> FEATURE:
<223> OTHER INFORMATION: Synthetic

<400> SEQUENCE: 5
ucaccaaaac auggaagcac uua                                           23

<210> SEQ ID NO 6
<211> LENGTH: 23
<212> TYPE: RNA
<213> ORGANISM: Artificial Sequence
<220> FEATURE:
<223> OTHER INFORMATION: Synthetic

<400> SEQUENCE: 6
acuuaaacgu ggauguacuu gcu                                           23

<210> SEQ ID NO 7
<211> LENGTH: 17
<212> TYPE: RNA
<213> ORGANISM: Artificial Sequence
<220> FEATURE:
<223> OTHER INFORMATION: Synthetic
```

```
<400> SEQUENCE: 7
uaagugcuuc cauguuu                                                   17

<210> SEQ ID NO 8
<211> LENGTH: 23
<212> TYPE: RNA
<213> ORGANISM: Artificial Sequence
<220> FEATURE:
<223> OTHER INFORMATION: Synthetic

<400> SEQUENCE: 8
uaagugcuuc cauguuuugg uga                                            23

<210> SEQ ID NO 9
<211> LENGTH: 23
<212> TYPE: RNA
<213> ORGANISM: Artificial Sequence
<220> FEATURE:
<223> OTHER INFORMATION: Synthetic

<400> SEQUENCE: 9
uaagugcuuc cauguuuag uag                                             23

<210> SEQ ID NO 10
<211> LENGTH: 23
<212> TYPE: RNA
<213> ORGANISM: Artificial Sequence
<220> FEATURE:
<223> OTHER INFORMATION: Synthetic

<400> SEQUENCE: 10
uaagugcuuc cauguucag ugg                                             23

<210> SEQ ID NO 11
<211> LENGTH: 23
<212> TYPE: RNA
<213> ORGANISM: Artificial Sequence
<220> FEATURE:
<223> OTHER INFORMATION: Synthetic

<400> SEQUENCE: 11
uaagugcuuc cauguuugag ugu                                            23

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
gaggctggag cagaaggatt gctttgg                                        27

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
ccctcctgac ccatcacctc caccacc                                        27
```

The invention claimed is:

1. A method for inducing CD34-positive adult stem cell (CD34+ASC) expansion and derivation in vitro, comprising:
    (a) providing at least a small RNA containing SEQ ID NO:7;
    (b) providing at least a wound healing-related defined factor containing LIF and bFGF/FGF2;
    (c) providing at least a CD34-positive adult stem cell (CD34+ASC); and
    (d) mixing the small RNA containing SEQ ID NO:7 of (a), the wound healing-related defined factor containing LIF and bFGF/FGF2 of (b), and the CD34+ASC of (c) together under an in-vitro cell culture condition to induce and maintain the expansion and derivation of CD34+ASCs.

2. The method as defined in claim 1, wherein said CD34+ASC are skin stem cells.

3. The method as defined in claim 1, wherein said CD34+ASC are isolated stem cells from skin tissues.

4. The method as defined in claim 1, wherein said CD34+ASC are originally located in skins.

5. The method as defined in claim 1, wherein said CD34+ ASCs are transplanted and form adult stem cell niches or pouches in vivo.

6. The method as defined in claim 1, wherein said CD34+ ASCs are differentiated into skin-associated skin tissue cell types after changing cell culture conditions in vitro as well as after transplantation.

7. The method as defined in claim 1, wherein said small RNA containing SEQ ID NO:7 contains at least a hairpin-like stem-loop structure.

8. The method as defined in claim 1, wherein said small RNA containing SEQ ID NO:7 contains at least a microRNA precursor.

9. The method as defined in claim 1, wherein said small RNA containing SEQ ID NO:7 is miR-302 precursor (pre-miR-302).

10. The method as defined in claim 1, wherein said small RNA containing SEQ ID NO:7 is a combination of SEQ ID NO:1, SEQ ID NO:2, SEQ ID NO:3, and SEQ ID NO:4.

11. The method as defined in claim 1, wherein said small RNA containing SEQ ID NO:7 is miR-302 mimic siRNA.

12. The method as defined in claim 1, wherein said small RNA containing SEQ ID NO:7 can be further processed into mature miR-302 in the CD34+ASCs.

13. The method as defined in claim 1, wherein said wound healing-related defined factor containing LIF and bFGF/FGF2 further includes stem cell factor (SCF).

14. The method as defined in claim 1, wherein said in-vitro cell culture condition is a feeder-free MSC expansion culture medium at 37° C.

15. The method as defined in claim 1, wherein said in-vitro cell culture condition further contains cell culture gel.

16. The method as defined in claim 1, wherein said CD34+ ASCs are transplanted in a patient in need of wound healing.

* * * * *